(12) United States Patent
Ogawa

(10) Patent No.: US 8,878,146 B2
(45) Date of Patent: Nov. 4, 2014

(54) MEDICAL IMPLANTS

(75) Inventor: Takahiro Ogawa, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 1582 days.

(21) Appl. No.: 11/885,474

(22) PCT Filed: Mar. 3, 2006

(86) PCT No.: PCT/US2006/008327
§ 371 (c)(1),
(2), (4) Date: Jul. 15, 2009

(87) PCT Pub. No.: WO2006/096793
PCT Pub. Date: Sep. 14, 2006

(65) Prior Publication Data
US 2009/0283701 A1    Nov. 19, 2009

Related U.S. Application Data

(60) Provisional application No. 60/659,449, filed on Mar. 7, 2005, provisional application No. 60/700,830, filed on Jul. 19, 2005, provisional application No. 60/707,688, filed on Aug. 12, 2005, provisional application No. 60/713,697, filed on Sep. 2, 2005.

(51) Int. Cl.
*B82Y 40/00* (2011.01)
*A61F 2/28* (2006.01)
(Continued)

(52) U.S. Cl.
CPC .......... *A61F 2/30767* (2013.01); *A61B 17/866* (2013.01); *A61L 24/02* (2013.01); *A61L 24/046*
(Continued)

(58) Field of Classification Search
USPC ................ 250/492.1; 219/121.67–121.69; 623/16.11–23.62; 977/901, 904, 919
See application file for complete search history.

(56) References Cited

U.S. PATENT DOCUMENTS 5,635,089 A * 6/1997 Singh et al. .............. 219/121.69
6,143,037 A   11/2000 Goldstein et al.
(Continued)

FOREIGN PATENT DOCUMENTS

JP   08-257110    10/1996
JP   2005-505352   2/2005

OTHER PUBLICATIONS

Wang et al., 'Photogeneration of Highly Amphiphilic TiO2 Surfaces', 1998, Advanced Materials, vol. 10, No. 2, p. 135-138.*

(Continued)

*Primary Examiner* — Phillip A Johnston
*Assistant Examiner* — Eliza Osenbaugh-Stewar
(74) *Attorney, Agent, or Firm* — DLA Piper LLP (US)

(57) ABSTRACT

Provided herein is methods of treating a medical implant and methods of using the same.

15 Claims, 35 Drawing Sheets

(51) Int. Cl.
- *A61F 2/30* (2006.01)
- *A61B 17/86* (2006.01)
- *A61L 24/02* (2006.01)
- *A61L 24/04* (2006.01)
- *A61L 24/06* (2006.01)
- *A61L 27/50* (2006.01)
- *A61L 31/14* (2006.01)
- *B23K 26/00* (2014.01)
- A61B 17/68 (2006.01)
- A61B 17/80 (2006.01)
- A61C 8/02 (2006.01)
- A61F 2/00 (2006.01)
- A61F 2/18 (2006.01)
- A61F 2/32 (2006.01)
- A61F 2/36 (2006.01)
- A61F 2/38 (2006.01)
- A61F 2/42 (2006.01)
- A61F 2/44 (2006.01)

(52) U.S. Cl.
CPC ........ (2013.01); *A61L 24/06* (2013.01); *A61L 27/50* (2013.01); *A61L 31/14* (2013.01); *B23K 26/0084* (2013.01); B82Y 40/00 (2013.01); A61B 17/68 (2013.01); A61B 17/80 (2013.01); A61C 8/0006 (2013.01); A61F 2/0077 (2013.01); A61F 2/186 (2013.01); A61F 2/2803 (2013.01); A61F 2/3094 (2013.01); A61F 2/32 (2013.01); A61F 2/36 (2013.01); A61F 2/38 (2013.01); A61F 2/4261 (2013.01); A61F 2/44 (2013.01); A61F 2002/183 (2013.01); A61F 2002/30031 (2013.01); A61F 2002/30062 (2013.01); A61F 2002/3084 (2013.01); A61F 2002/30906 (2013.01); A61F 2002/30925 (2013.01); A61F 2002/3097 (2013.01); A61F 2002/3625 (2013.01); A61F 2210/0004 (2013.01); A61F 2250/0056 (2013.01); A61F 2310/00011 (2013.01); A61F 2310/00017 (2013.01); A61F 2310/00023 (2013.01); A61F 2310/00029 (2013.01); A61F 2310/00041 (2013.01); A61F 2310/00047 (2013.01); A61F 2310/00059 (2013.01); A61F 2310/00071 (2013.01); A61F 2310/00089 (2013.01); A61F 2310/00095 (2013.01); A61F 2310/00107 (2013.01); A61F 2310/00131 (2013.01); A61F 2310/00149 (2013.01); A61F 2310/00155 (2013.01); A61F 2310/00179 (2013.01); A61F 2310/00293 (2013.01); A61F 2310/00329 (2013.01); A61F 2310/00353 (2013.01); A61L 2400/12 (2013.01); A61L 2400/18 (2013.01); Y10S 977/901 (2013.01); Y10S 977/904 (2013.01)
USPC ............. 250/492.1; 623/16.11; 977/901; 977/904

(56) References Cited

U.S. PATENT DOCUMENTS

| | | | | |
|---|---|---|---|---|
| 7,442,629 | B2 * | 10/2008 | Mazur et al. | 438/487 |
| 2004/0000540 | A1 | 1/2004 | Soboyejo | |
| 2004/0145053 | A1 | 7/2004 | Auner et al. | |
| 2004/0153154 | A1 * | 8/2004 | Dinkelacker | 623/16.11 |
| 2004/0210309 | A1 * | 10/2004 | Denzer et al. | 623/16.11 |
| 2005/0019371 | A1 | 1/2005 | Anderson | |
| 2005/0064007 | A1 * | 3/2005 | Steinemann et al. | 424/423 |
| 2005/0211680 | A1 | 9/2005 | Li et al. | |
| 2006/0247793 | A1 * | 11/2006 | Trieu et al. | 623/23.76 |
| 2006/0275339 | A1 * | 12/2006 | Schilke et al. | 424/426 |

OTHER PUBLICATIONS

Wang et al. 'Light Induced Amphilic Surfaces', Jul. 31, 1997, Nature, vol. 388, p. 431-432.*

Bundy et al., 'The Effect of Surface Prepartion on Metal/Bone Cement Interfacial Strength', 1987, Journal of Biomedical Materials Research, vol. 21, p. 773-805.*

Zubkov et al. 'Ultraviolet Light-Induced Hydrophilicity Effect on $TiO_2(110)(1X1)$. Dominant Role of the Photooxidation of Adsorbed Hydrocarbons Causing Wetting by Water Droplets' Jul. 27, 2005, Journal of Physical Chemistry B, vol. 109, pp. 15454-15462.*

Japanese Notice of Reasons for Refusal issued by JPO on Nov. 30, 2010, in connection with Appl. No. 2008-500895, 4 pgs.

Translation of Japanese Notice of Reasons for Refusal issued by JPO on Nov. 30, 2010, in connection with Appl. No. 2008-500895, 2 pgs.

Supplementary European Search Report for EP 06737494, mailed Jan. 27, 2009, 7 pgs.

* cited by examiner

Machined

Before / After

Acid-etched Ti

Before / After

Machined

Acid-etched Ti

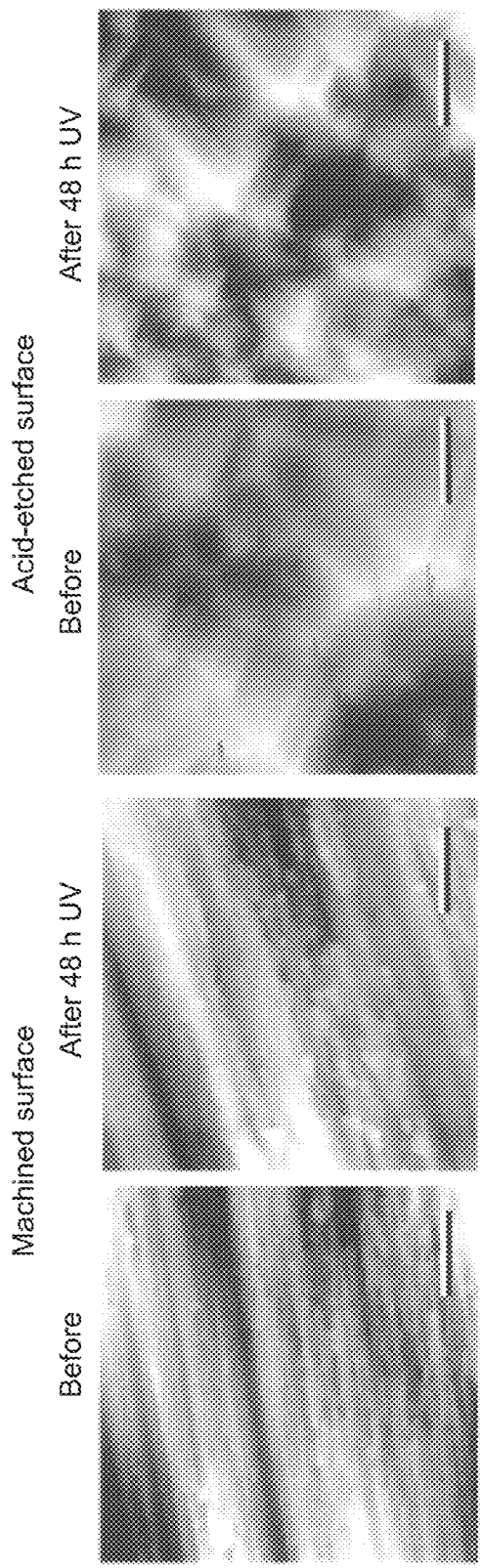
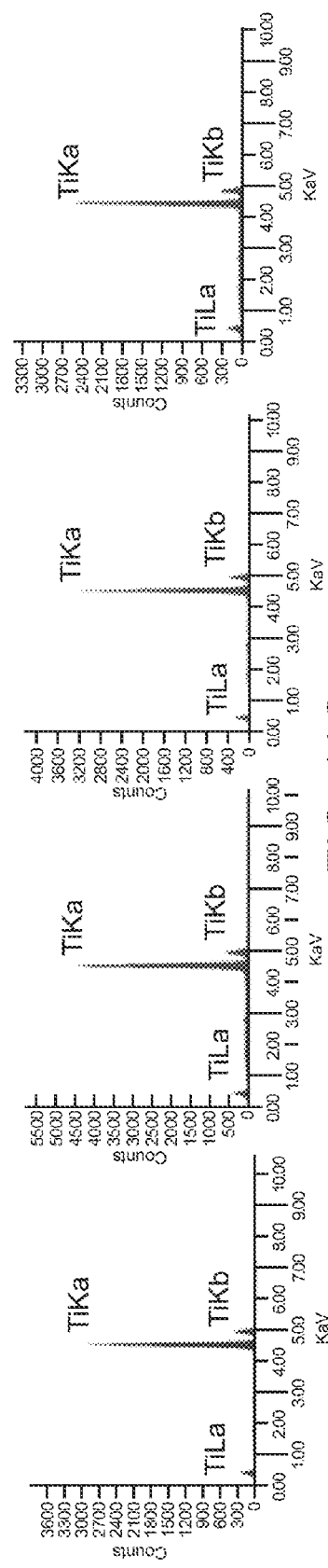
FIG. 10B
FIG. 10C

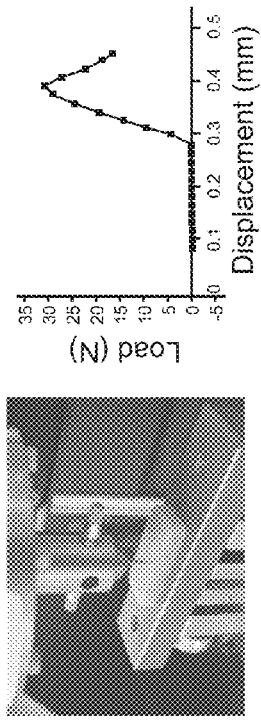
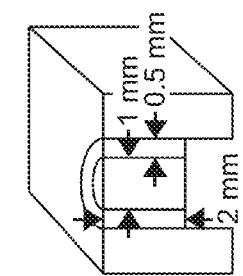
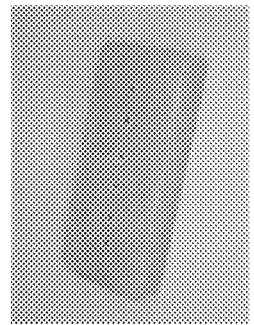
FIG. 16A  FIG. 16B  FIG. 16C  FIG. 16D
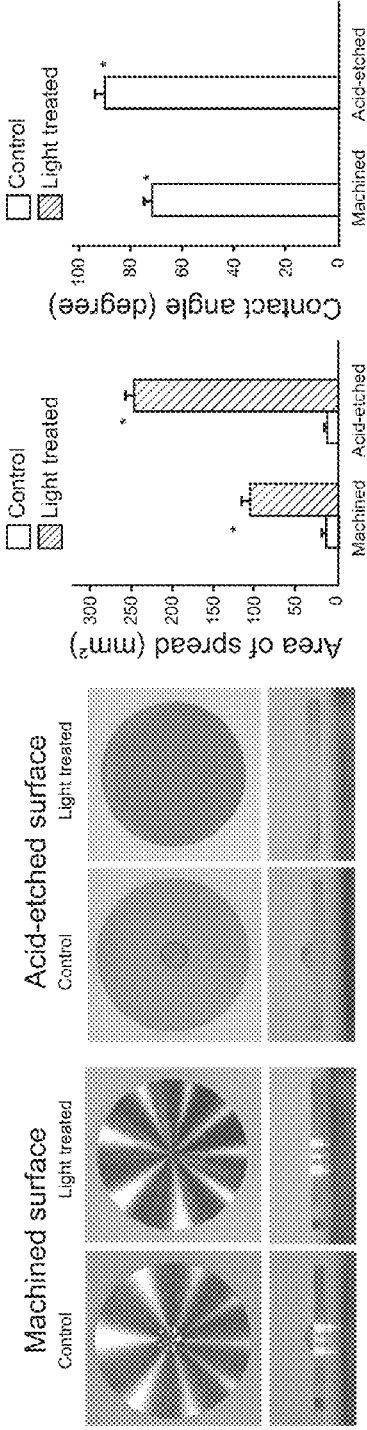
FIG. 17

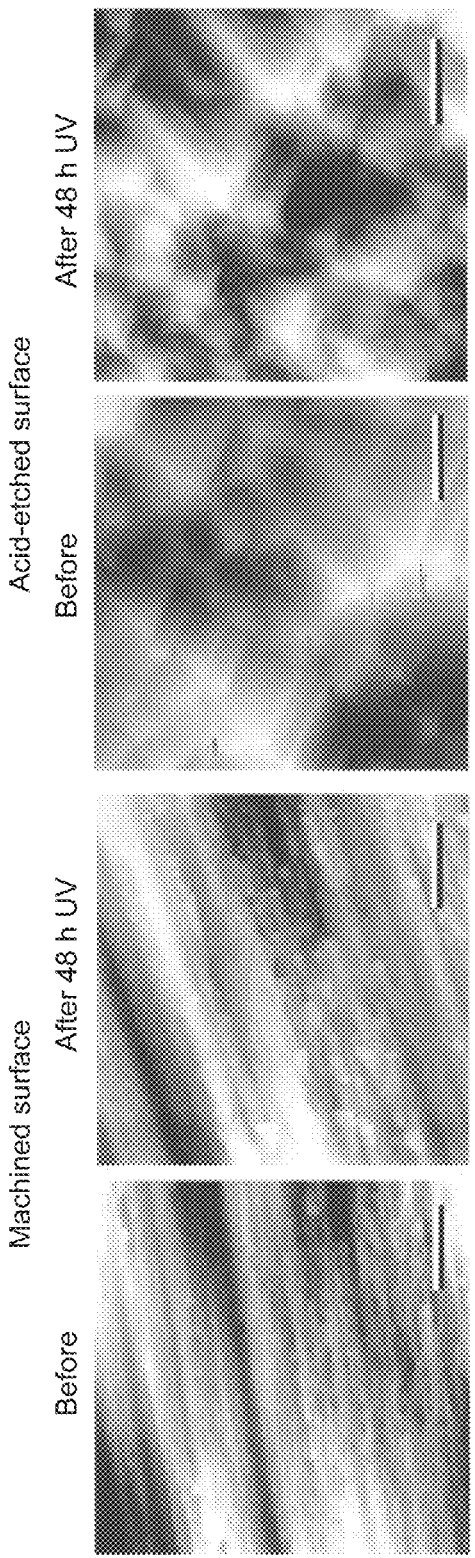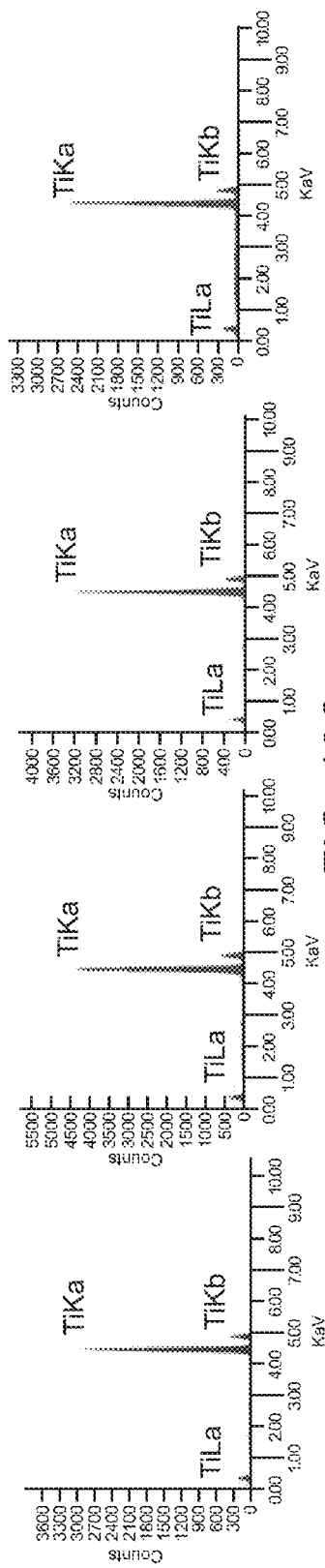
FIG. 18B
FIG. 18C

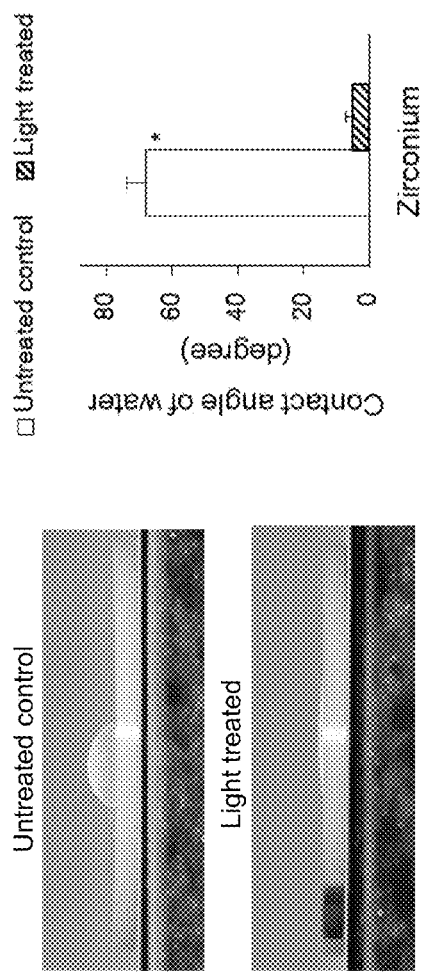
FIG. 24A
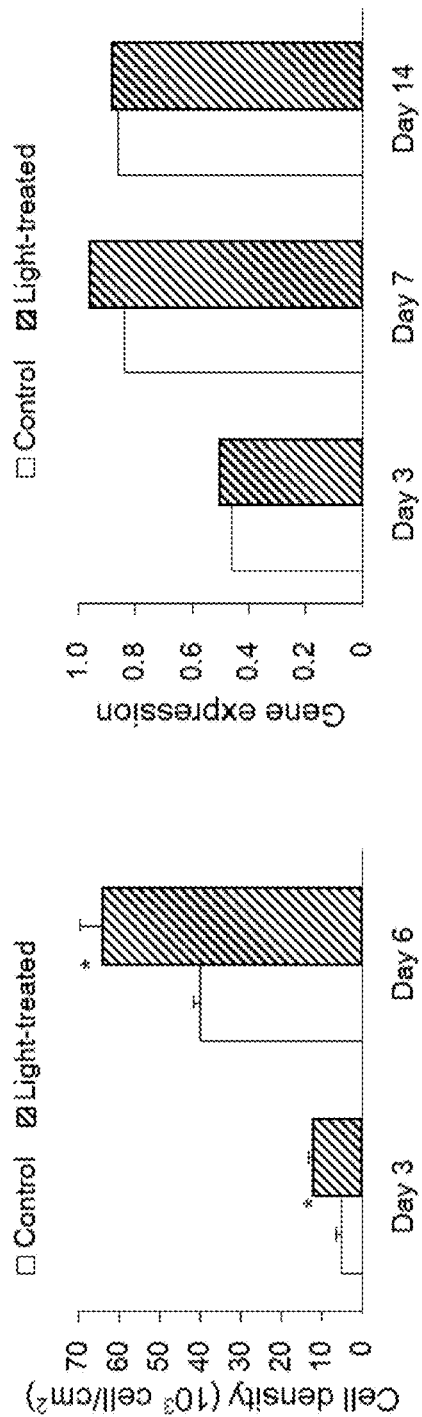
FIG. 24B
FIG. 24C

MEDICAL IMPLANTS

CROSS-REFERENCE TO RELATED APPLICATIONS

This invention is a US national stage entry of International Application No. PCT/U.S.2006/08327 filed Mar. 3, 2006, which claims the benefit of U.S. Provisional Application No. 60/659,449 filed Mar. 7, 2005, of U.S. Provisional Application No. 60/700,830 filed Jul. 19, 2005, of U.S. Provisional Application No. 60/707,688 filed Aug. 12, 2005, and of U.S. Provisional Application No. 60/713,697 filed Sep. 2, 2005, each of which is hereby incorporated by reference in its entirety.

BACKGROUND OF THE INVENTION

1. Field of the Invention

This invention generally relates to a metallic implant for biomedical use. In particular, the present invention relates to medical implants with enhanced capability for tissue-to-implant and bone cement-to-implant integration.

2. Description of the Background

Restoration of skeletal defects or wounds such as femoral neck fracture and spine fusion is a common procedure. For example, over 500,000 and 250,000 procedures are performed annually in the U.S. for hip prosthesis implantation and spine fusion surgery, respectively. Meanwhile, about 74 million people in the U.S., which amounts to about 30% of adult population in the U.S., have at least one qradrant of posterior missing tooth that needs to be restored.

Some metallic materials such as titanium are proven biocompatible materials. For example, use of titanium implants has become a standard treatment to replace missing teeth and to fix diseased, fractured or transplanted bone. Restorative treatment of missing teeth using dental implants such as titanium implants have considerable oral health impact, by which masticatory function (Carlsson G E, Lindquist L W, Int. J. Prosthodont 7(5):448-53 (1994); Geertman M E, et al., Community Dent Oral Epidemiol 24(1):79-84 (1996); Pera P, et al., J Oral Rehabil 25(6):462-7 (1998); van Kampen F M, et al., J Dent Res 83(9):708-11 (2004)), Speech (Heydecke G, et al., J Dent Res 83(3):236-40 (2004)) and daily performance and quality of life (Melas F, et al., Int J Oral Maxillofac Implants 16(5):700-12 (2001)) are improved, when compared to the conventional removable denture treatment. In treatments of facial defect resulting from cancer or injury, the use of endosseous implants is crucial to retain the prosthesis (Roumanas E D, et al., Int J Prosthodont 15(4):325-32 (2002)). However, the application of implant therapy in these fields is still limited because of various risk factors including anatomy and quality of host bone (van Steenberghe D, et al., Clin Oral Implants Res 13(6):617-22 (2002)), systemic conditions including diabetes (Nevins M L, Int J Oral Maxillofac Implants 13(5):620-9 (1998); Takeshita F, et al., J Periodontol 69(3):314-20 (1998) and osteoporosis (Ozawa S, et al., Bone 30(1):13743 (2002)), and ageing (Takeshita F, et al., J Biomed Mater Res 34(1):1-8 (1997)). More importantly, long healing time (about 4-10 months) required for titanium implants to integrate with surrounding bone restricts the application of this beneficial treatment. For example, in the U.S., dental implant therapy has penetrated into only 2% of the potential patients.

In the orthopedic field, the restoration of femoral neck fracture or spine fusion, for example, is a common problem. For example, of over 250,000 procedures performed annually in the U.S. for spine fusion surgery, about 30% or more of patients fail to achieve a solid bony union. The nature and location of bone fracture at these areas do not allow for bone immobilization (e.g., cast splinting) for better healing.

Therefore, there is a need for faster and stronger fixation of bone by metallic implants. There is also a need for stronger bone cement-metallic implant interfacial strength. The embodiments described below address the above identified issues and needs.

SUMMARY OF THE INVENTION

Provided herein are methods of treating medical implants for enhancing the tissue integration capabilities and/or enhanced bone cement-metallic implant interfacial strength of the medical implants. The method includes applying a high energy radiation to a medical implant to cause the medical implant to generate a surface having nanostructural topography. The medical implant can include metallic and/or non-metallic materials and can optionally include a cement composition. The nanostructural topography can include nanoconstructs such as nanospheres, nanocones, nanopyramids, other nanoconstructs or combinations thereof. In some embodiments, the nanoconstructs have a size in the range between about 1 nm and about 500 nm, between about 1 nm and about 200 nm, between about 1 nm and about 100 nm, between about 10 nm and about 100 nm, between about 10 nm and about 70 nm, between about 20 nm and about 50 nm or between about 20 nm and about 40 nm.

The medical implants can be metallic implants or non-metallic implants. In some embodiments, the medical implants are metallic implants such as titanium implants, e.g., titanium implants for replacing missing teeth (dental implants) or fixing diseased, fractured or transplanted bone. Other exemplary metallic implants include, but are not limited to, titanium alloy implants, chromium-cobalt alloy implants, platinum and platinum alloy implants, nickel and nickel alloy implants, stainless steel implants, zirconium, chromium-cobalt alloy, gold or gold alloy implants, and aluminum or aluminum alloy implants.

The medical implants or devices described herein can be made by a process that includes applying a high energy radiation to the medical implants. The medical implants provided herein can be used to treat, prevent, ameliorate, or reduce symptoms of a medical condition such as missing teeth, a need for orthodontic anchorage or bone related medical conditions such as femoral neck fracture, neck bone fracture, wrist fracture, spine fracture/disorder or spinal disk displacement, fracture or degenerative changes of joints such as knee joint arthritis, bone and other tissue defect or recession caused by a body condition or disorder such as cancer, injury, systemic metabolism, infection and aging, limb amputation resulting from injuries and diseases, and combinations thereof.

The implants provided herein can be subjected to various established surface treatments to increase surface area or surface roughness for better tissue integration or tissue attachment. Representative surface treatments include, but are not limited to, physical treatments and chemical treatments. Physical treatments include, e.g., machined process, sandblasting process, metallic deposition, non-metallic deposition (e.g., apatite deposition), or combinations thereof. Chemical treatment includes, e.g., etching using a chemical agent such as an acid, base (e.g., alkaline treatment), oxidation, and combinations thereof. For example, a metallic implant can form different surface topographies by a machined process or an acid-etching process.

BRIEF DESCRIPTION OF DRAWINGS

FIG. 1a shows the scanning electron micrographs (Bar=20 μm). FIG. 1b shows the atomic force micrographs. FIG. 1c shows the energy dispersive spectroscopic elemental analysis.

FIG. 2a shows a hydrophobic surface before UV irradiation and a highly hydrophilic surface on UV irradiated surface. FIG. 2b shows an oleophobic surface before UV irradiation that changed into a highly oleophilic surface after UV irradiation, evaluated by 10 μl droplets of glycerol. FIG. 2c shows a highly hemophilic surface of UV irradiated titanium surface, evaluated by 50 μl droplets of blood extracted from the rat aorta.

FIGS. 10a-10c show the surface morphology and elemental composition of titanium surfaces used in this study, before and after ultra violet UV light treatment.

FIGS. 16a-16d show the preparation of the titanium samples for push-put test.

FIG. 17 shows ultraviolet UV light-induced changes of wettability of titanium surfaces having two different surface topographies; machined and acid-etched surfaces.

FIGS. 18a-18c show surface morphology and elemental composition of titanium surfaces used in this study, before and after ultra violet UV light treatment.

FIGS. 24A, 24B and 24C show ultraviolet UV light-induced improvement of water wettability of machined zirconium oxide surfaces.

DETAILED DESCRIPTION

Figure 1A:
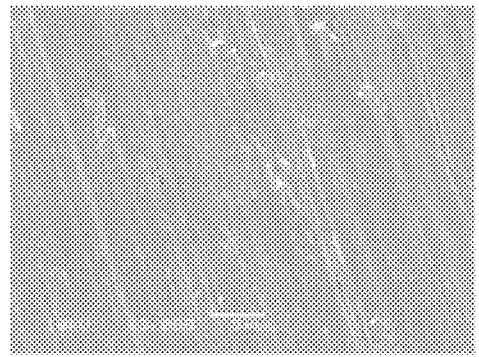
FIGS. 1a-1c show the surface morphology and element of titanium surfaces used in the study of Example 1 (machined surface and acid-etched surface).
Figure 1A:
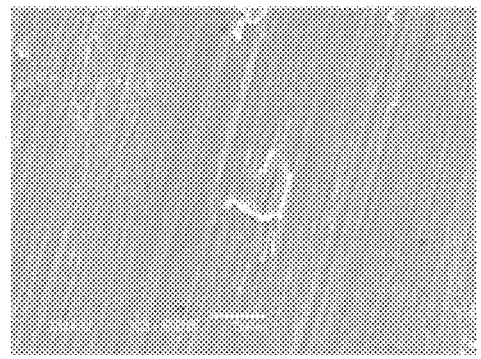
Figure 1A:
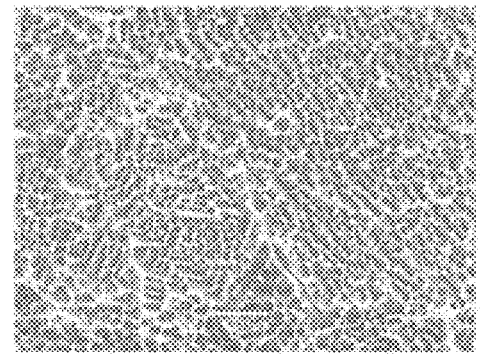
Figure 1A:
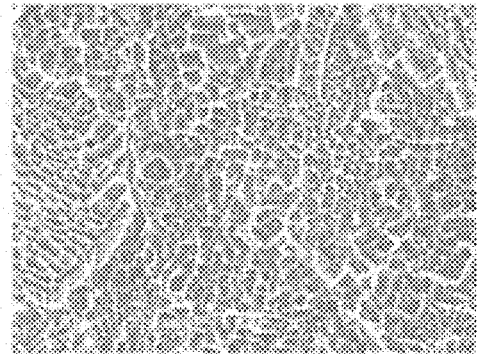

Provided herein are methods of treating medical implants for enhancing the tissue integration capabilities and/or enhanced bone cement-metallic implant interfacial strength of the medical implants. The method includes applying a high energy radiation to a medical implant to cause the medical implant to generate a surface having nanostructural topography. The medical implant can include metallic and/or non-metallic materials and can optionally include a cement composition. The nanostructural topography can include nanoconstructs such as nanospheres, nanocones, nanopyramids, other nanoconstructs or combinations thereof. In some embodiments, the nanoconstructs have a size in the range between about 1 nm and about 500 nm, between about 1 nm and about 200 nm, between about 1 nm and about 100 nm, between about 10 nm and about 100 nm, between about 10 nm and about 70 nm, between about 20 nm and about 50 nm or between about 20 nm and about 40 nm.

As used herein, the term "tissue integration capability" refers to the ability of a medical implant to be integrated into the tissue of a biological body. The tissue integration capability of an implant can be generally measured by several factors, one of which is wettability of the implant surface, which reflects the hydrophilicity/oleophilicty (hydrophobicity), or hemophilicity of an implant surface. Hydrophilicity and oleophilicity are relative terms and can be measured by, e.g., water contact angle (Oshida Y, et al., J Mater Science 3:306-312 (1992)), and area of water spread (Gifu-kosen on line text, http://www.gifu-nct.ac.jp/elec/tokoro/fft/contact-angle.html). For purposes of the present invention, the hydrophilicity/oleophilicity can be measured by contact angle or area of water spread of an implant surface described herein relative to the ones of the control implant surfaces. Relative to the implant surfaces not treated with the process described herein, a medical implant treated with the process described herein has a substantially lower contact angle or a substantially higher area of water spread.

The medical implants can be metallic implants or non-metallic implants. In some embodiments, the medical implants are metallic implants such as titanium implants, e.g., titanium implants for replacing missing teeth (dental implants) or fixing diseased, fractured or transplanted bone. Other exemplary metallic implants include, but are not limited to, titanium alloy implants, chromium-cobalt alloy implants, platinum and platinum alloy implants, nickel and nickel alloy implants, stainless steel implants, zirconium, chromium-cobalt alloy, gold or gold alloy implants, and aluminum or aluminum alloy implants.

The medical implants or devices described herein can be made by a process that includes applying a high energy radiation to the medical implants. The medical implants provided herein can be used to treat, prevent, ameliorate, or reduce symptoms of a medical condition such as missing teeth, a need for orthodontic anchorage or bone related medical conditions such as femoral neck fracture, neck bone fracture, wrist fracture, spine fracture/disorder or spinal disk displacement, fracture or degenerative changes of joints such as knee joint arthritis, bone and other tissue defect or recession caused by a body condition or disorder such as cancer, injury, systemic metabolism, infection and aging, limb amputation resulting from injuries and diseases, and combinations thereof.

The implants provided herein can be subjected to various established surface treatments to increase surface area or surface roughness for better tissue integration or tissue attachment. Representative surface treatments include, but are not limited to, physical treatments and chemical treatments. Physical treatments include, e.g., machined process, sandblasting process, metallic deposition, non-metallic deposition (e.g., apatite deposition), or combinations thereof. Chemical treatment includes, e.g., etching using a chemical agent such as an acid, base (e.g., alkaline treatment), oxidation, and combinations thereof. For example, a metallic implant can form different surface topographies by a machined process or an acid-etching process.

As used herein, the term "light treatment" can be used interchangeably with the term "light activation," "light radiation," "light irradiation," "UV light activation," "UV light radiation" or "UV light irradiation."

Medical Implants

The medical implants described herein with enhanced tissue integration capabilities include any implants currently available in medicine or to be introduced in the future. The implants can be metallic or non-metallic implants. Non-metallic implants include, for example, ceramic implants, calcium phosphate or polymeric implants. Useful polymeric implants can be any biocompatible implants, e.g., bio-degradable polymeric implants. Representative ceramic implants include, e.g., bioglass and silicon dioxide implants. Calcium phosphate implants includes, e.g., hydroxyapatite, tricalciumphosphate (TCP). Exemplary polymeric implants include, e.g., poly-lactic-co-glycolic acid (PLGA), polyacrylate such as polymethacrylates and polyacrylates, and polylactic acid (PLA) implants. In some embodiments, the medical implant described herein can specifically exclude any of the aforementioned materials.

In some embodiments, the implant comprises a metallic implant and a bone-cement material. The bone cement material can be any bone cement material known in the art. Some representative bone cement materials include, but are not limited to, polyacrylate or polymethacrylate based materials such as poly(methyl methacrylate) (PMMA)/methyl methacrylate (MMA), polyester based materials such as PLA or PLGA, bioglass, ceramics, calcium phosphate-based materials, calcium-based materials, and combinations thereof. In some embodiments, the medical implant described herein can specifically exclude any of the aforementioned materials.

The metallic implants described herein include titanium implants and non-titanium implants. Titanium implants include tooth or bone replacements made of titanium or an alloy that includes titanium. Titanium bone replacements include, e.g., knee joint and hip joint prostheses, femoral neck replacement, spine replacement and repair, neck bone replacement and repair, jaw bone repair, fixation and augmentation, transplanted bone fixation, and other limb prostheses. None-titanium metallic implants include tooth or bone implants made of gold, platinum, tantalum, niobium, nickel, iron, chromium, cobalt, magnesium, magnesium, aluminum, palladium, zirconium, chromium-cobalt alloy, alloy formed thereof, e.g., stainless steel, or combinations thereof. In some embodiments, the metallic implant can specifically exclude any of the aforementioned metals.

The medical implant described herein can be porous or non-porous implants. Porous implants can impart better tissue integration while non-porous implants can impart better mechanical strength.

High Energy Radiation

The medical implants with enhanced tissue integration capabilities provided herein can be formed by treating the medical implants with a high energy radiation for a period of time. The length of the radiation period depends on the type of implants. For a metallic implant (e.g., a titanium implant), the period of radiation generally ranges from about 1 minute to about 1 month, e.g., from about 1 minute to about 1 hour, from about 1 hour to about 5 hours, from about 5 hours to about 24 hours, from about 1 day to about 5 days, from about 5 days to about 10 days, or from about 10 days to about 1 month. For non-metallic implants, e.g., a biocompatible, biodurable polymeric implant, the period of radiation generally ranges about 1 minute to about 1 month, e.g., from about 1 minute to about 1 hour, from about 1 hour to about 5 hours, from about 5 hours to about 24 hours, from about 1 day to about 5 days, from about 5 days to about 10 days, or from about 10 days to about 1 month.

The term "high energy radiation" includes radiation by light or a magnetic wave. In some embodiments, the term "high energy" refers to a radiation having a wavelength at or below about 400 nm, e.g., about 350 nm, about 300 nm, about 250 nm, about 200 nm, about 150 nm, about 100 nm, about 50 nm, or about 10 nm.

In some embodiments, the radiation can have a wavelength at or below about 5 nm, about 1 nm, about 0.5 nm, about 0.1 nm, about 0.05, about 0.01, about 0.005 or about 0.001 nm. The radiation having a wavelength from about 400 nm to 10 nm is generally referred to as ultraviolet light UV, the radiation having a wavelength from about 10 nm to 0.1 nm is generally referred to as x-rays, and the radiation having a wavelength from about 0.1 nm to about 0.001 nm is generally referred to as gamma-rays.

The medical implants can be radiated with or without sterilization. To one of ordinary skill in the art, the medical implants can be sterilized during the process of high energy radiation (e.g., UV radiation).

In anther aspect of the present invention, it is provided a facility or device for radiating medical implants. In one embodiment, the facility or device includes a chamber for placing medical implants, a source of high energy radiation and a switch to switch on or turn off the radiation. The facility or device may further include a timer. In some embodiments, the facility or device can further include a mechanism to cause the medical implants or the high energy radiation source to turn or spin for full radiation of the implants. Alternatively, the chamber for placing medical implants can have a reflective surface so that the radiation can be directed to the medical implants from different angles, e.g., 360° angle. In some embodiments, the facility or device may include a preservation mechanism of the enhanced bone-integration capability, e.g., multiple irradiation of light, radio-lucent implant packaging, packing and shipping.

Medical Use

The medical implants provided herein can be used for treating, preventing, ameliorating, correcting, or reducing the symptoms of a medical condition by implanting the medical implants in a mammalian subject. The mammalian subject can be a human being or a veterinary animal such as a dog, a cat, a horse, a cow, a bull, or a monkey.

Representative medical conditions that can be treated or prevented using the implants provided herein include, but are not limited to, missing teeth or bone related medical conditions such as femoral neck fracture, missing teeth, a need for orthodontic anchorage or bone related medical conditions such as femoral neck fracture, neck bone fracture, wrist fracture, spine fracture/disorder or spinal disk displacement, fracture or degenerative changes of joints such as knee joint arthritis, bone and other tissue defect or recession caused by a disorder or body condition such as, e.g., cancer, injury, systemic metabolism, infection or aging, and combinations thereof.

EXAMPLES

The embodiments of the present invention will be illustrated by the following set forth examples. All parameters and data are not to be construed to unduly limit the scope of the embodiments of the invention.

Example 1

Bone Generation by Light-Induced Super-Amphiphilic Titanium Implants

Methods

Titanium Samples, Surface Analysis and Ultraviolet UV Light Irradiation

Two surface types of commercially pure titanium were prepared for cylindrical implants (1 mm in diameter and 2 mm in length) and disks (20 mm in diameter and 1.5 mm in thickness). One had a machined surface, turned by a lathe. The other was dual acid-etched with $H_2SO_4$ and HCl (Osseotite®; Implant Innovations, West Palm Beach, Fla.). The titanium disks were sterilized by gamma radiation. Surface morphology was examined by scanning electron microscopy (SEM) (JSM-5900LV, Joel Ltd, Tokyo, Japan) and atomic force microscopy (SPM-9500J3, Shimadzu, Tokyo, Japan). The average roughness (Ra), root mean square roughness (Rrms) and peak-to-valley (Rp-v) were calculated. Titanium discs and implants were irradiated with UV at a level of 0.1 mW/cm² UVA and 0.03 mW/cm² UVB for 48 hours with air ventilation.

Wet Ability of Titanium Surface

The contact angle and spread area of distilled water (hydrophilicity test) and glycerol (oleophilicity test). Additionally, blood extracted from rat aorta was used. Ten μl of distilled water and glycerol were gently deposited on the titanium surface and digitally photographed immediately. The spread area was measured as the area of the drop in the top view using a digital analyzer (Image Pro Plus, Media Cybernetics, Silver Spring, Md.). The contact angle θ were obtained by the equation: $\theta = 2\tan^{-1}(2h/d)$, where h and d are the height and diameter of the drop in the side view.

Cell Culture

Bone marrow cells isolated from the femur of 8-week-old male Sprague-Dawley rats were placed into alpha-modified Eagle's medium supplemented with 15% fetal bovine serum, 50 mg/ml ascorbic acid, $10^{-8}$M dexamethasone and Antibiotic-antimycotic solution containing 10000 units/ml Penicillin G sodium, 10000 mg/ml Streptomycin sulfate and 25 mg/ml Amphotericin B. Cells were incubated in a humidified atmosphere of 95% air, 5% $CO_2$ at 37° C. At 80% confluency, the cells were detached using 0.25% Trypsin-1 mM EDTA-4Na and seeded onto either the machined titanium or acid-etched titanium disks at a density of $5 \times 10^4$ cells/cm² in the above mentioned medium with 10 mM Na-β-glycerophosphate. The culture medium was renewed every three days. To examine the effect of UV irradiated titanium on fibroblastic behaviors, NIH3T3 cells were cultured.

Proliferation Assay

The cells were gently rinsed twice with PBS and treated with 0.1% collagenase in 300 μl of 0.25% trypsin-1 mM EDTA-4Na for 15 min at 37° C. A hematocytometer was used to count the number of detached cells. Selected substrates were examined under scanning electron microscopy to confirm there were no remaining cells.

Gene Expression Analysis

Steady-state gene expression was analyzed using the reverse transcription-polymerase chain reaction (RT-PCR). Total RNA in the cultures was extracted using TRIzol (Invitrogen, Carlsbad, Calif.) and purification column (RNeasy, Qiagen, Valencia, Calif.). Following DNAse I treatment, reverse transcription of 0.5 μg of total RNA was performed using MMLV reverse transcriptase (Clontech, Carlsbad, Calif.) in the presence of oligo(dT) primer (Clontech, Carlsbad, Calif.). The PCR reaction was performed using Taq DNA polymerase (EX Taq, Takara Bio, Madison, Wis.) to detect alpha-I type I collagen, osteopontin, and osteocalcin mRNA. The primer sequences and PCR conditions are described in Supplementary 2. Resulting products were visualized on 1.5% agarose gel with ethidium bromide staining. The intensity of bands was quantified under UV light (Eagle Eye II, Strategene, La Jolla, Calif.). The values were normalized with reference to GAPDH mRNA.

Mineralization Assay

The mineralized cultures were rinsed three times with distilled water and dried over night and photographed. Digital images were processed to subtract background color using digital imaging software (Adobe Photoshop 5.0, Adobe, San Jose, Calif.). The processed images were analyzed by a digitized image analysis system (Image Pro-plus, Media Cybernetics, MD) for the mineral nodule area defined as (white area/total well area)×100(%).

Animal Surgery

Five 8-week-old male Sprague-Dawley rats were anesthetized with 1-2% isoflurane inhalation. After their legs were shaved and scrubbed with 10% providone-iodine solution, the distal aspects of the femurs were exposed via skin incision and muscle dissection. The flat surfaces of the distal femurs were selected for implant placement. The implant site was prepared 11 mm from the distal edge of the femur by drilling with a 0.8 mm round burr followed by reamers #ISO 090 and 100. Profuse irrigation with sterile isotonic saline solution was used for cooling and cleaning. One untreated cylindrical implant and one UV irradiated implant were placed into the right and left femurs, respectively. Implant stability was confirmed with a passive mechanical fit. Surgical sites were then closed in layers. Muscle and skin were sutured separately with resorbable suture thread. The University of California at Los Angeles (UCLA) Chancellor's Animal Research Committee approved this protocol and all experimentation was performed in accordance with the United States Department of Agriculture (USDA) guidelines of animal research.

Implant Biomechanical Push-in Test

This method to assess biomechanical strength of bone-implant integration is described elsewhere (Ogawa T, et al., J Dent Res 79(11):1857-63 (2000)). Briefly, femurs containing a cylindrical implant were harvested and embedded immediately in auto-polymerizing resin with the top surface of the implant level. The testing machine (Instron 5544 electromechanical testing system, Instron, Canton, Mass.) equipped with a 2000 N load cell and a pushing rod (diameter=0.8 mm) was used to load the implant vertically downward at a crosshead speed of 1 mm/min. The push-in value was determined by measuring the peak of load-displacement curve.

Other Metallic Surfaces Tested for UV-Induced Hydrophilicity

To address the UV-induced hydrophilicity on different surface types and on other metals, three different surface characteristics of commercially pure titanium, and machined surfaces of titanium and chromium-cobalt alloys were prepared. Three different titanium surfaces other than the machined and acid-etched surfaces were a deposited titanium surface using an electron beam evaporator, a sandblasted surface with aluminum oxide particles and an oxidized surface by heating at 600° C.

Statistical Analysis

T-test was used to examine differences between the untreated control and UV irradiated experimental group; <0.05 was considered statistically significant.

Results

Figure 1B:
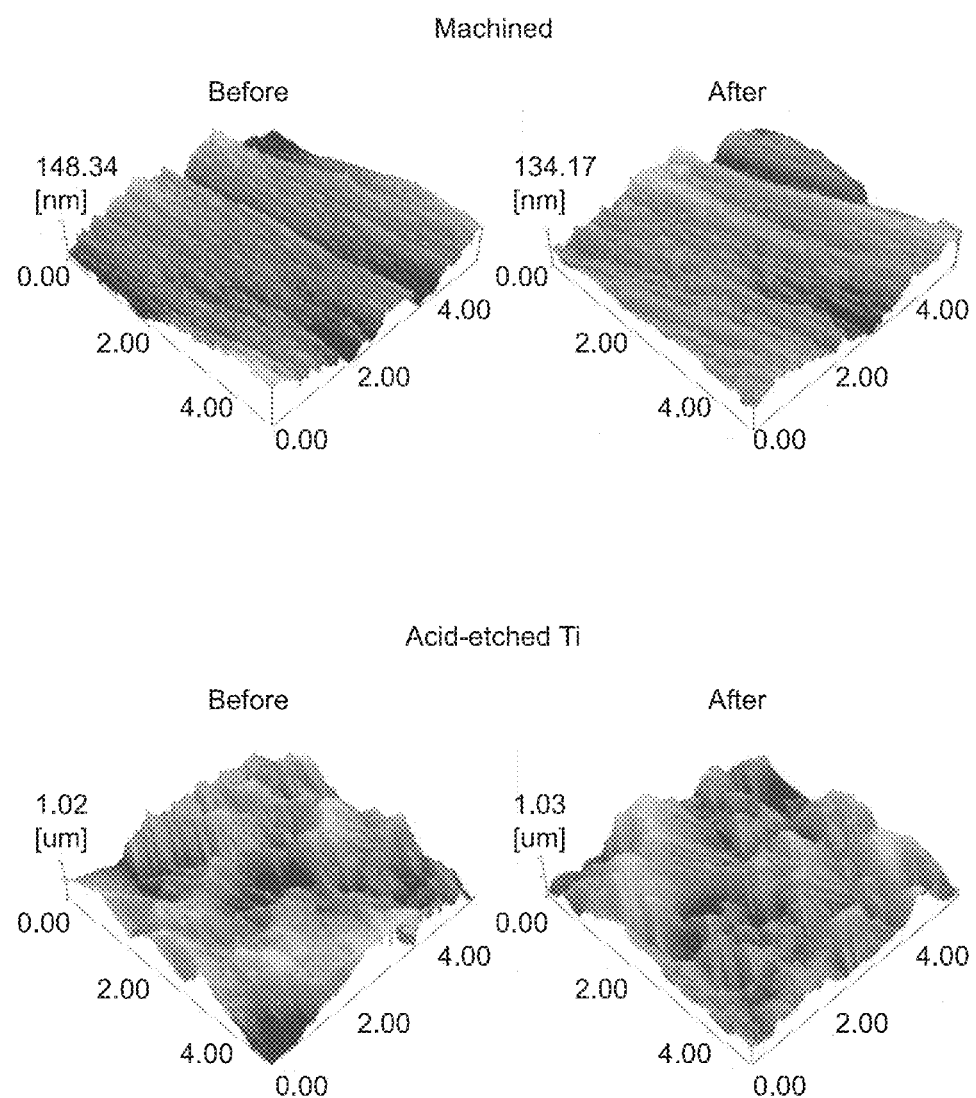
Figure 1C:
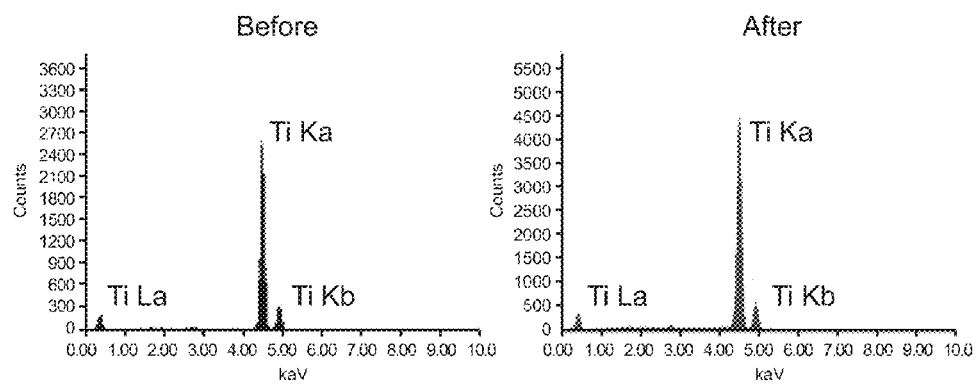
Figure 1C:
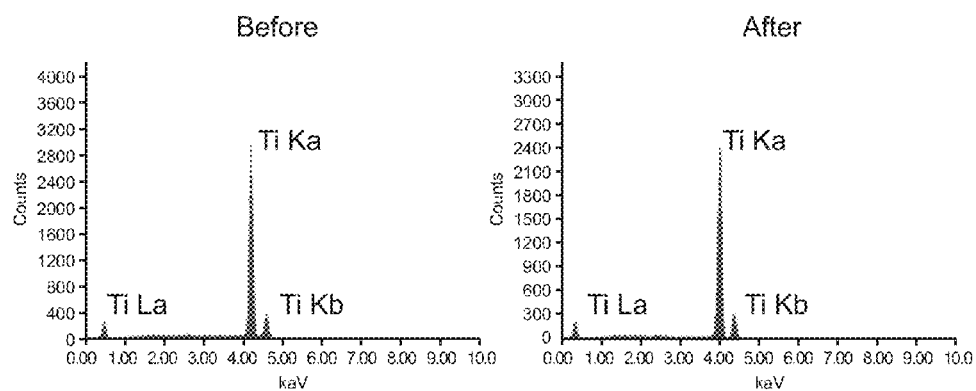

Two different surface topographies of titanium were prepared: machined surface and acid-etched surface. SEM examination showed isotropically and concentrically turned ridges on the machined surface (FIG. 1a), whereas the acid-etched surface displayed a uniformly roughened surface. AFM images depicted the smooth, wavy surface of the machined surface and micron- and sub-micron level roughness of the acid-etched surface (FIG. 1b). Both surface types were composed of commercially pure Ti with no contamination as shown by an energy dispersive X-ray (EDX) analysis (FIG. 1c). The average roughness (Ra), root mean square roughness (Rrms) and peak-to-valley roughness (Rp-v) were 24.4±5.1 nm, 30±8.2 nm, and 194.0±42 nm, respectively, for the machined surface, and 257.6±43.2 nm, 301.6±50.5 nm, and 1988.7±554.9 nm, respectively, for the acid-etched surface. In FIGS. 1a-1c, the UV irradiation was given at a level of 0.1 mW/cm$^2$ UVA and 0.03 mW/cm$^2$ UVB for 48 hours.

Figure 2A:
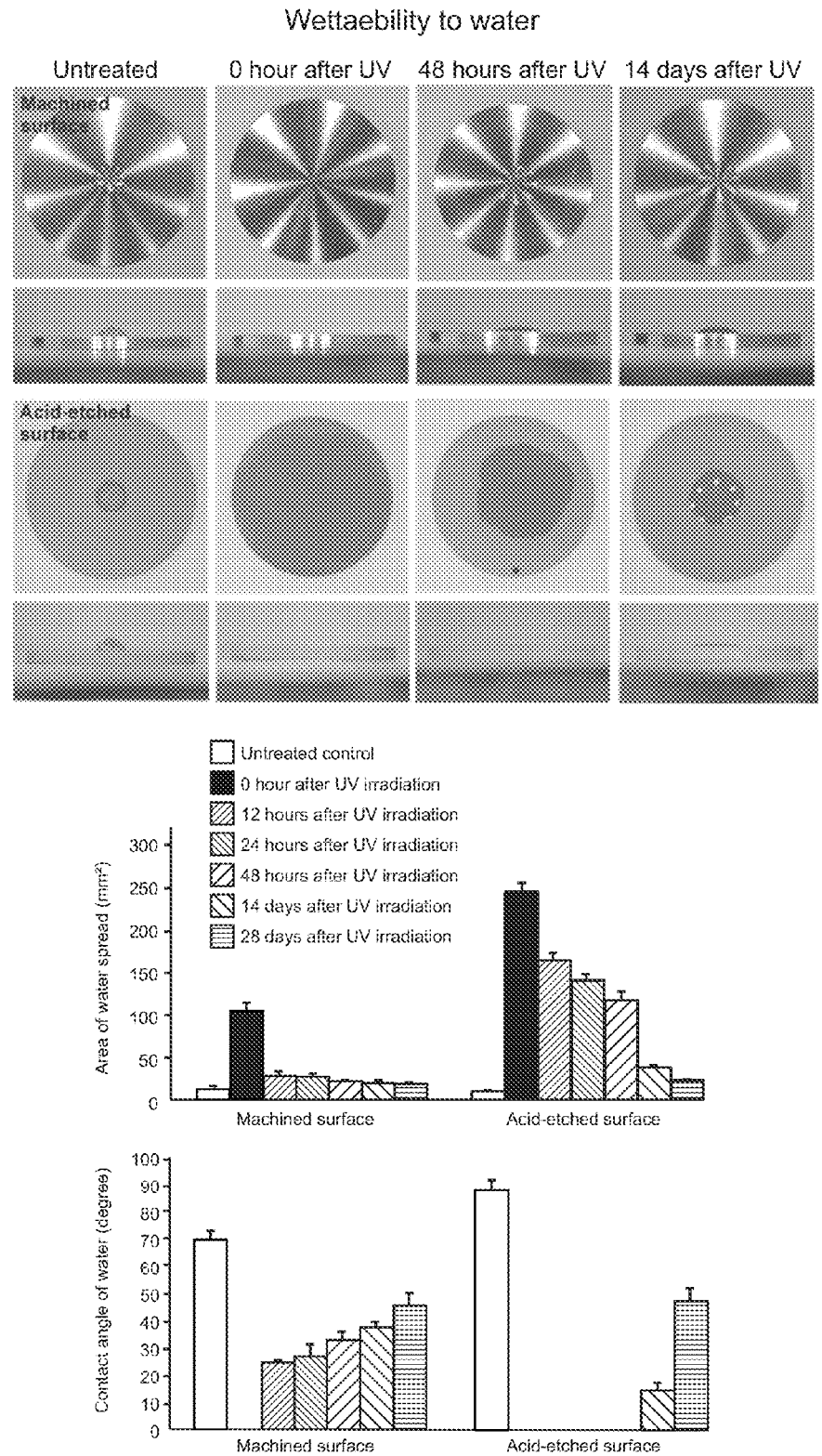
FIGS. 2a-2c show an ultraviolet light (UV)-induced dramatic changes of wettability on titanium surfaces having two different surface topographies.
Figure 2B:
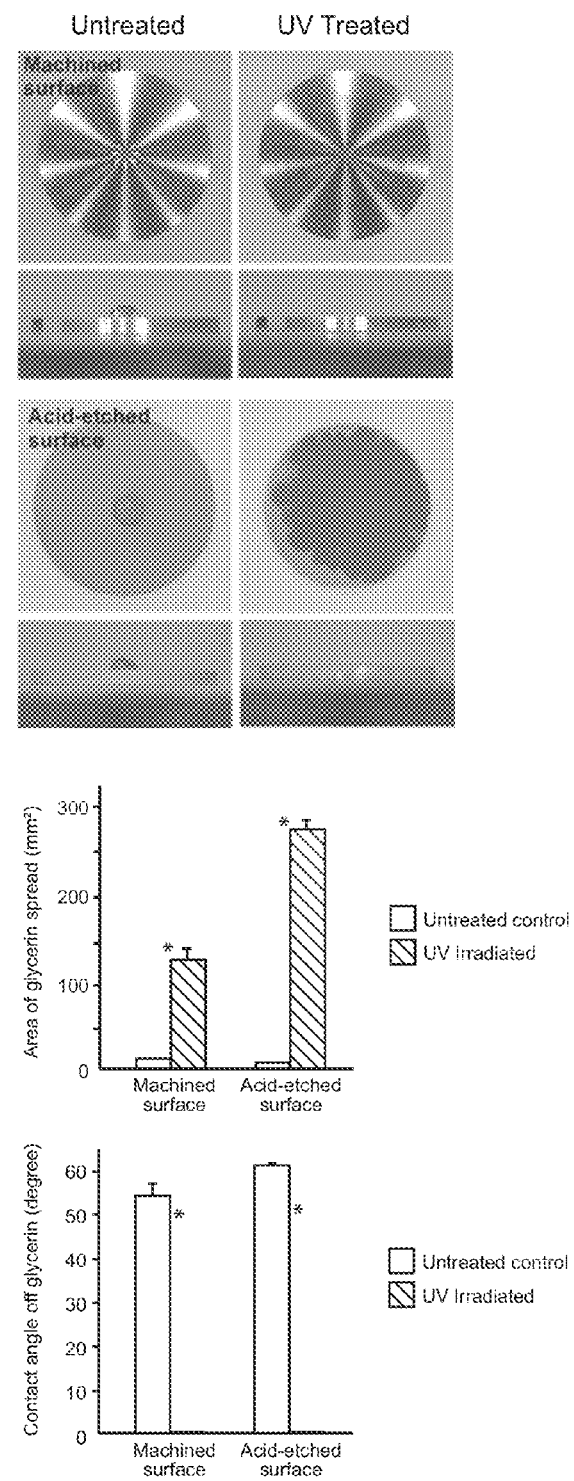
Figure 2C:
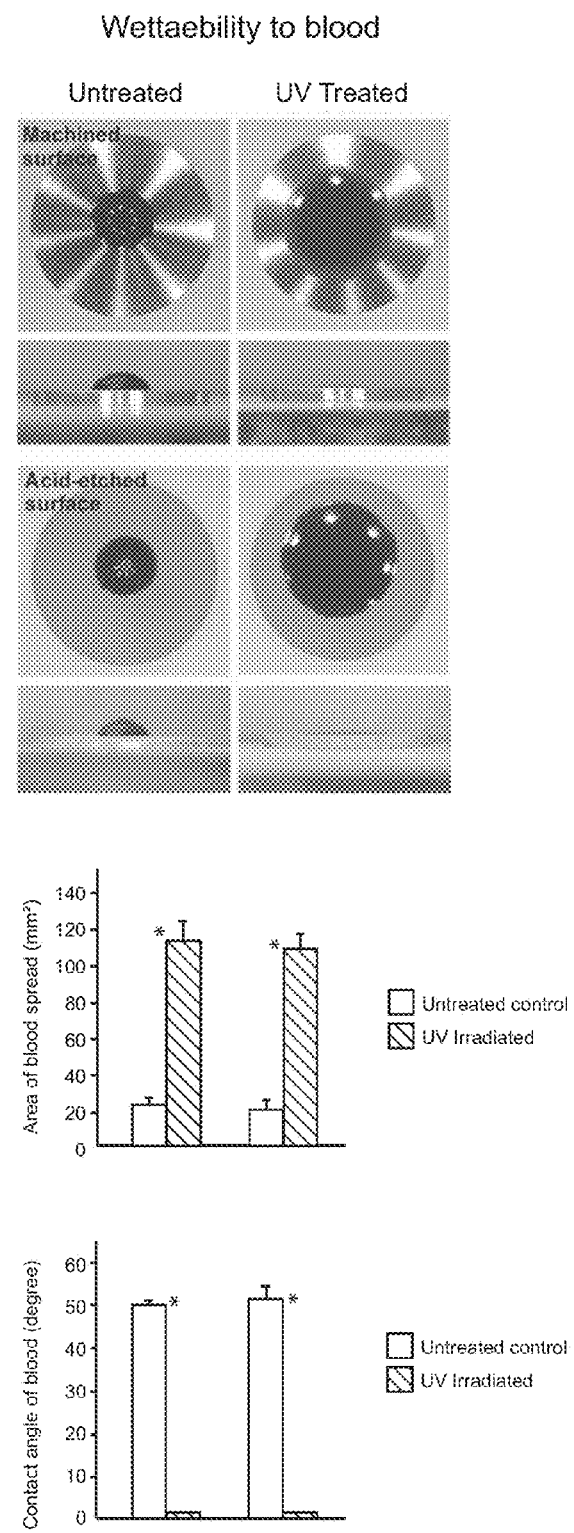

The changes in wettabilities (hydrophilicity, oleophilicity and hemophilicity) of titanium surfaces and their preservation were examined. It was evident that the spread area of 10 μl water drop dramatically increased after UV irradiation for both machined (13 times) and acid-etched surface (30 times) (FIG. 2a). As shown in FIG. 2a, a time-dependent preservation of the hydrophilicity is also presented. The hydrophilicity was evaluated by the spread area (the top views of the droplets) and the contact angle (the side views of the droplets) of 10 μl droplets of distilled water. Note that the contact angle was 0.0±0.0° after UV irradiation on the both surface topographies. The contact angle of water before irradiation, which was 69.9° and 88.4° for the machined and acid-etched surface, respectively, plummeted to 0.0±0.0° after UV irradiation. The UV-induced hydrophilicity was diluted as the time passed, and was more effective and sustained for the acid-etched surface than for the machine surface. The hydrophilicity represented by spread area was over 2 times and 4 times for the machined and acid-etched surfaces, respectively, after two weeks of the irradiation. The hydrophilicity, measured by water spread, of the acid-etched surface was twice as great as the control even after 4 weeks. A dramatic gain of oleophilicity using 10 μl drop of glycerol (FIG. 2b) and of hemophilicity using 50 μl drop of blood (FIG. 2c) for both surface types was also found, confirming the establishment of UV-generated highly amphiphilic (both hydrophilic and oleophilic) surfaces of titanium. In FIGS. 2a-2c, the symbol "*" indicates that the data are statistical significant between the UV irradiated and non treated control, p<0.0001.

Figure 3A:
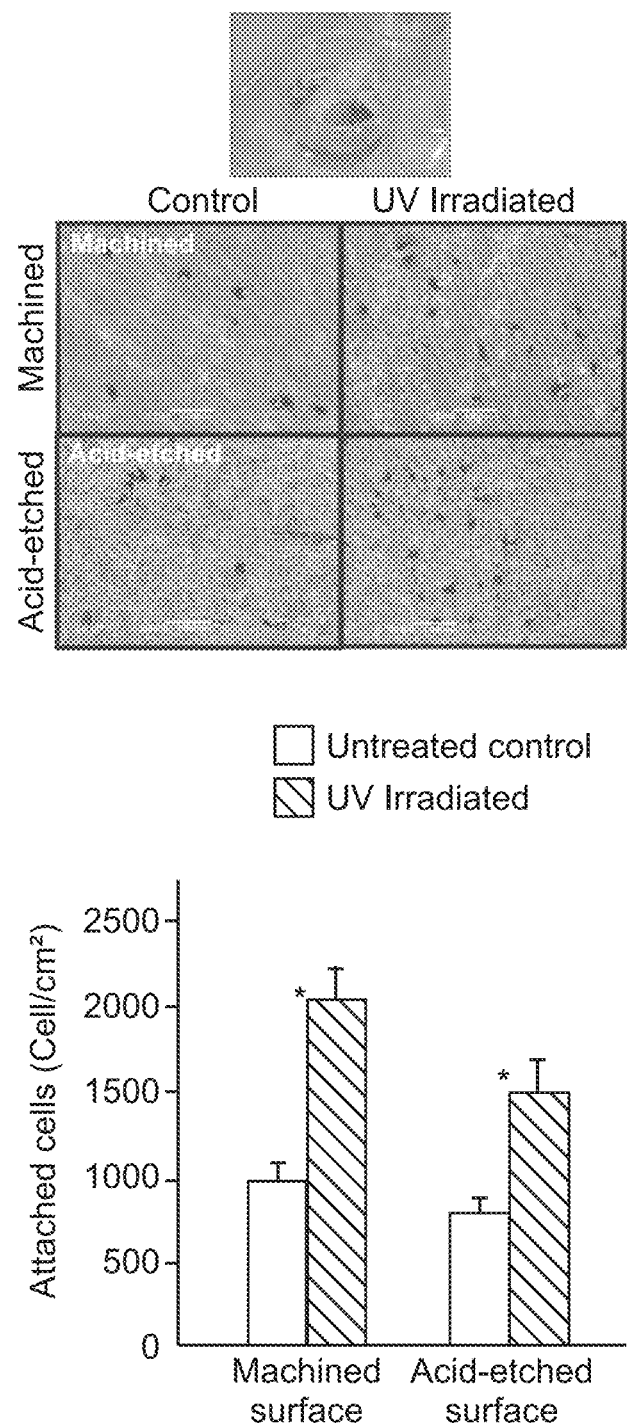
FIGS. 3a and 3b show an increased cell chemotaxis and cell proliferative activities of titanium, respectively, by the ultra-violet light irradiation on titanium.

The UV-induced amphiphilic titanium for osteogenic potential by its cell-philicity (cell chemotaxis and cell spread), cell proliferative capability, gene expression of bone-related proteins, in vitro mineralizing potential, establishment of biomechanical stability of titanium implants and bone generation was tested. To evaluate the chemotactic potential of amphiphilic titanium, bone marrow stem cells (BMSCs) derived from rat bone marrow were seeded into the polystyrene dish with titanium discs were set up vertically, where the cells face the titanium surface largely to the lateral (FIG. 3a). In FIG. 3a, the bone marrow-derived osteoblastic cells were faced to the titanium surfaces which were set up vertically (upper left panel). The attached cells to the titanium surfaces with (upper right) or without (upper middle) UV irradiation were counted after 3 hours of incubation. More cells were attached to the UV-irradiated surface than to the control surface.

Figure 3B:
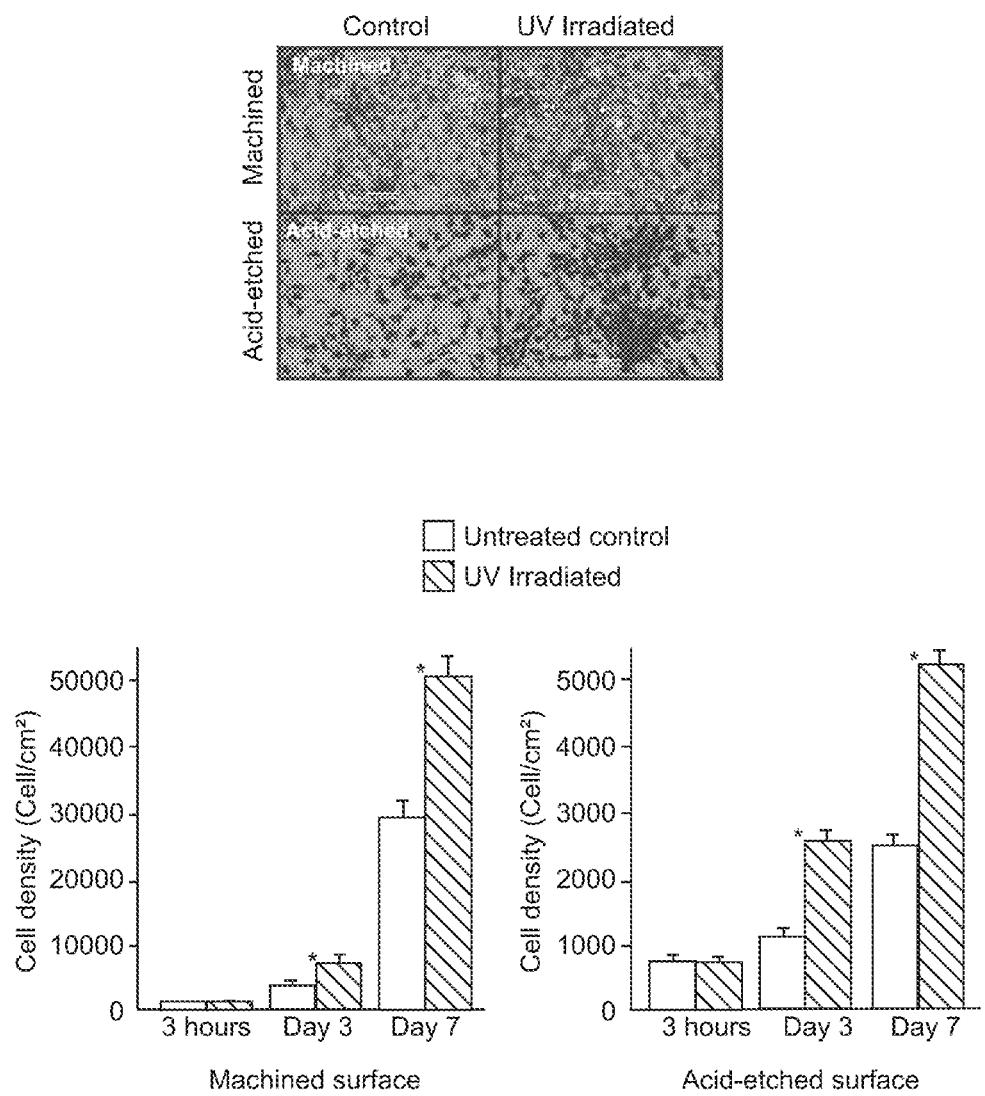

To evaluate the cell proliferation, BMSCs were inoculated onto the machined and acid-etched titanium discs horizontally placed in the polystyrene dish. UV irradiation facilitated the cell proliferation double on both surfaces at days 3 and 7 (FIG. 3b). In FIG. 3b, the cell density was defined as the number of cells in the cultures, where titanium discs were placed horizontally in the polystyrene culture dish. Data are shown as the mean±SD (n=3). The symbol "*" indicates that the data are statistically significant between the UV irradiated and non treated control, p<0.0001.

Figures 4A, 4B:
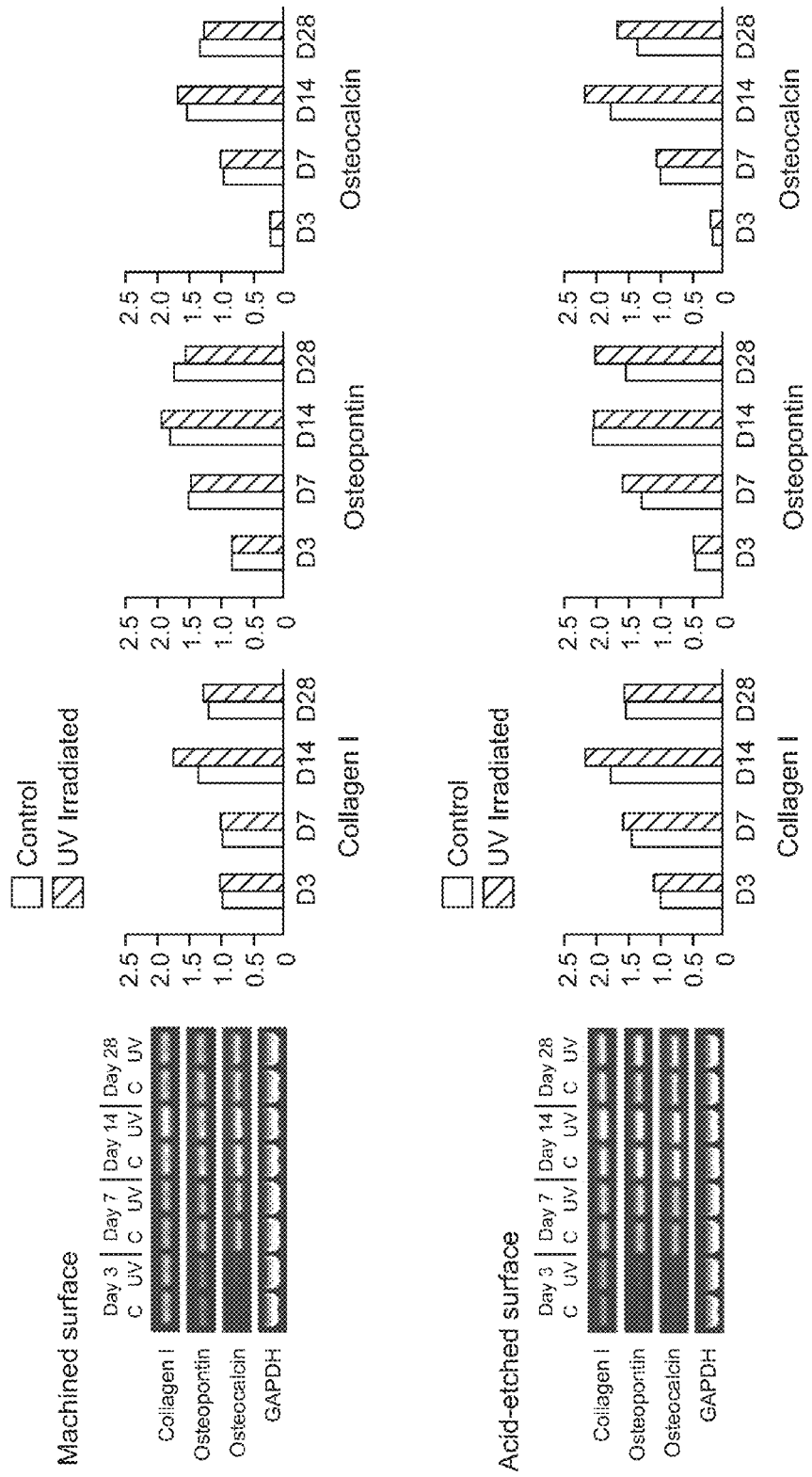
FIGS. 4a and 4b show the altered expression of bone-related genes after ultraviolet light irradiation on titanium.

The gene expression was examined by RT-PCR (reverse transcriptase-polymerase chain reaction) at several time points of the osteoblastic culture using BMSCs. The gene expression of collagen L osteopontin and osteocalcin were examined as the representative gene markers at the early, middle and late stages, respectively, of osteoblastic differentiation (FIGS. 4a and 4b). At all the time points of days 7, 14 and 28, the genes were upregulated on the UV irradiated titanium for both surface types, indicating the promoted differentiation of BMSCs into osteoblasts on the UV-generated amphiphilic titanium. FIG. 4a shows the images of reverse transcriptase-polymerase chain reaction (RT-PCR) visualized with ethidium bromide staining. The samples were obtained from the osteoblastic cultures on the machined titanium (top) and acid-etched titanium (bottom). FIG. 4b shows the quantified expression level and time course of the genes for the machined titanium (top) and acid-etched titanium (bottom) cultures. The intensity of bands were standardized by the level of GAPDH mRNA expression.

Figure 5:
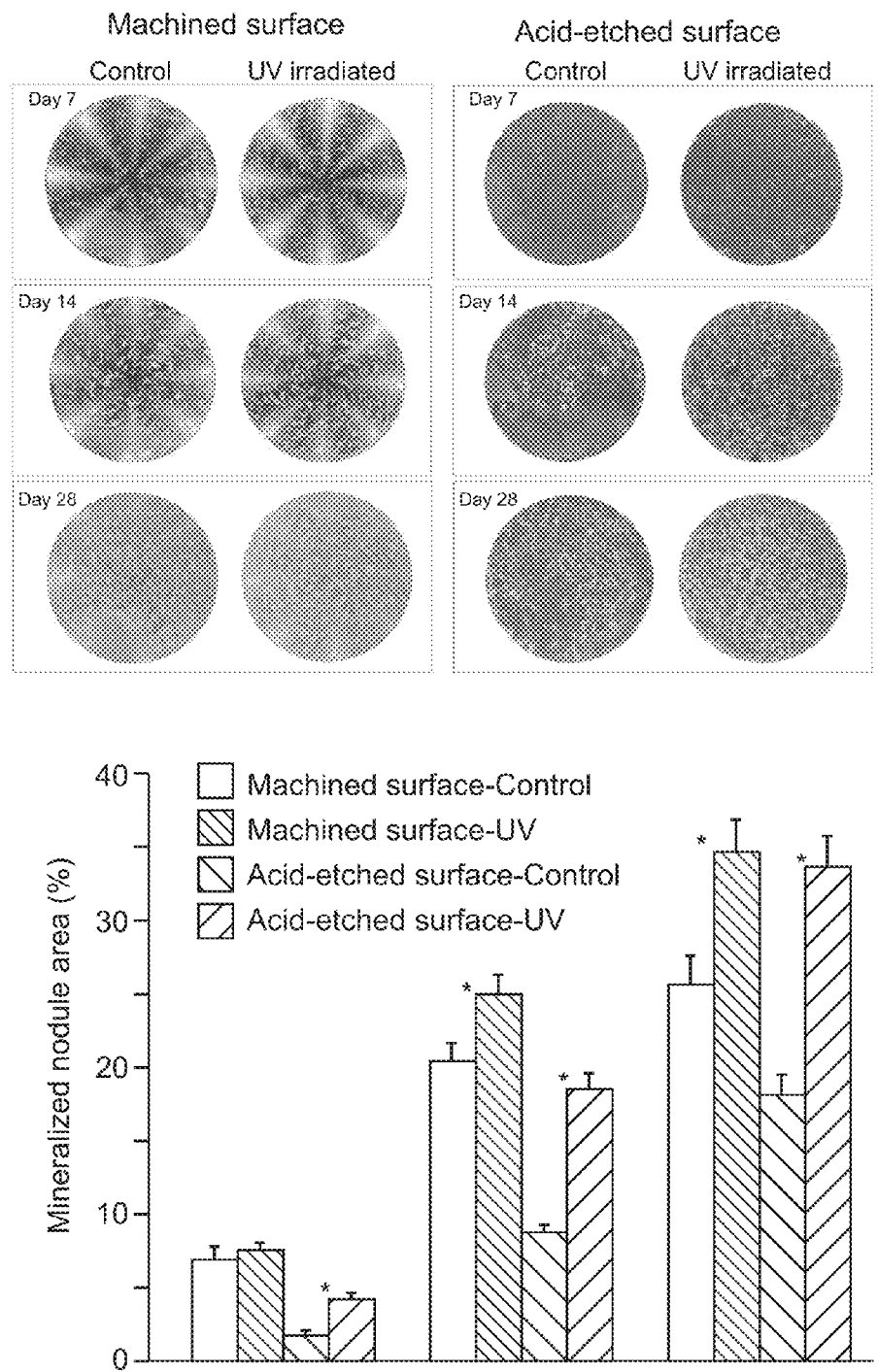
FIG. 5 shows the increased mineralizing ability of osteoblastic cultures by the ultra-violet UV light irradiation on titanium.

The effect of UV irradiation on the osteoblastic mineralizing potential was evaluated by the formation of mineralizing nodule in the BMSC/osteoblastic culture (FIG. 5). The increased area of mineralizing nodule after UV irradiation was found on both machined and acid-etched titanium surfaces: the UV effect was more remarkable for the acid-etched surface showing 100% to 150% increase. In FIG. 5, the upper panels show representative images of the dried mineralized cultures on the machined titanium surface and acid-etched titanium surface with or without UV irradiation, while the bottoms show the quantitative mineralized nodule area. The percentage of the mineralized nodule area relative to the culture area was measured using a digital image analyzer. Data are shown as the mean±SD (n=3). The symbol "*" indicates that the data are statistically significant between the UV irradiated and non treated control, p<0.0001.

Figure 6:
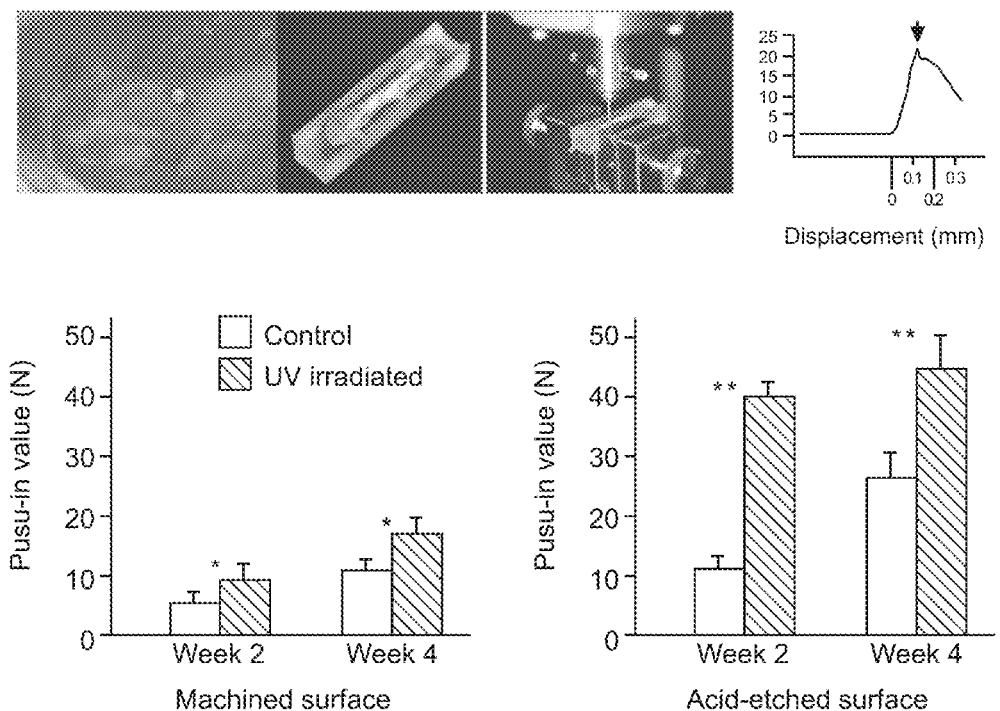
FIG. 6 shows the ultraviolet UV-enhanced bone-titanium integration evaluated by biomechanical push-in test for titanium implants with machined and acid-etched surfaces.

In vivo anchorage of titanium implants with or without UV irradiation was examined using the biomechanical implant push-in test FIG. 6). In the test shown by FIG. 6, titanium implants with or without UV irradiation were placed into the rat femur, and the biomechanical stability of the implants were evaluated at 2 and 4 weeks post-implantation by measuring the breakage strength against push-in load (top panel). Data are shown as the mean±SD (n=5). The symbol "*" indicates that the data are statistically significant between the UV irradiated and non treated control, p<0.05, while the symbol "**" indicates that the data are statistically significant between the UV irradiated and non treated control, p<0.0001. Implants placed into the rat femur were pushed-in vertically, and the force at a point of breakage (maximum force on the load-displacement curves) was measured as a push-in value. The push-in value at 2 weeks post-implantation soared 1.8 times and 3.1 times, respectively, for the machined surface and the acid-etched surface by UV irradiation. At week 4, the push-in value of the UV irradiated implants maintained the superiority over the untreated implants by 50% and 60%, respectively, for the machined surface and the acid-etched surface.

Figure 7:
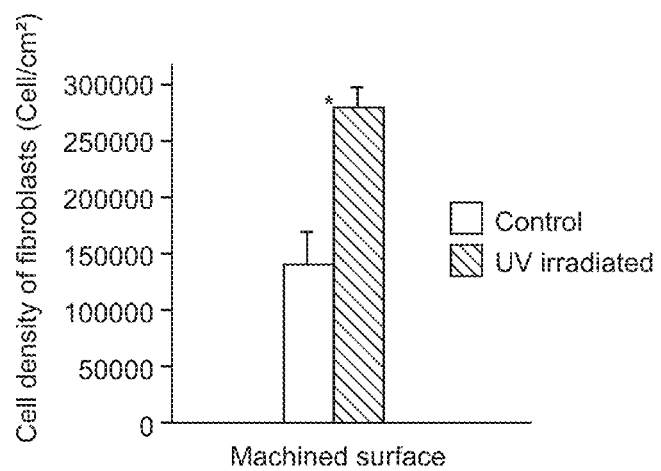
FIG. 7 shows an increased cell proliferative activity of fibroblasts by the ultra-violet light irradiation on titanium.

For the generation and preservation of bone around the body of titanium implants, the growth and preservation of soft tissue, such as epithelial and gingival tissues, around the neck area of implants are important for proper function and esthetics of dental implants. The UV-induced amphiphilic titanium was tested for its soft tissue growth potential by measuring the proliferation rate of fibroblasts. NIH3T3 fibroblasts were seeded onto the machined titanium discs with or without UV irradiation, and the cell density was evaluated after 3 days. The proliferation rate on the UV activated titanium was increased 100% compared to the one on the untreated control (FIG. 7). In FIG. 7, the attached NIH3T3 fibroblasts to the machined titanium surfaces with or without UV irradiation were counted after 3 hours of incubation. The cell density was defined as the number of cells in the cultures. Data are shown as the mean±SD (n=3). The symbol "*" indicates that the data are statistical significant between the UV irradiated and non treated control, p<0.0001.

Figure 8:
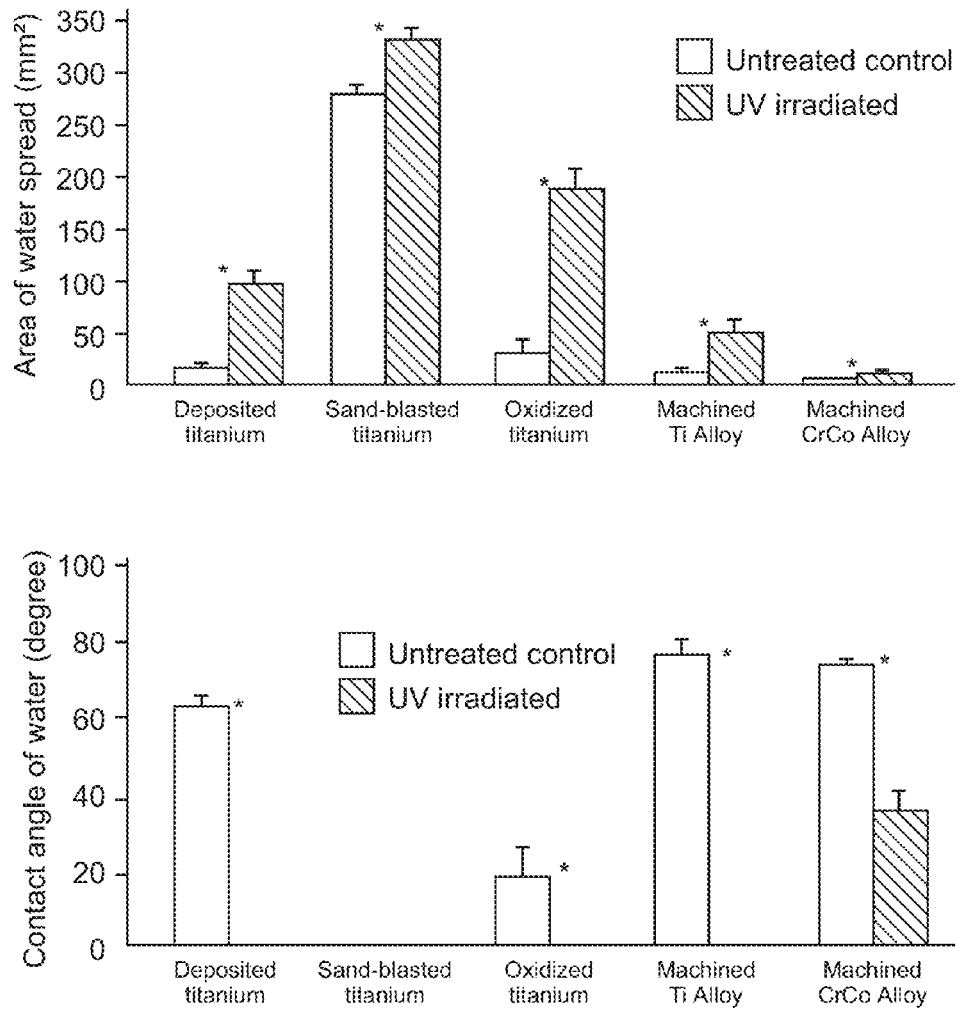
FIG. 8 shows an ultraviolet light-induced dramatic increase of wettability on titanium surfaces having various surface characteristics and on other metals.

To address the UV-induced hydrophilicity on different surface types and on other metals, three different surface characteristics of commercially pure titanium, and machined surfaces of titanium and chromium-cobalt alloys were prepared and tested. UV irradiation induced highly hydrophilic surfaces on the deposited titanium surface, sand blasted titanium surface, oxidized titanium surface, machined titanium alloy surface and machined chromium-cobalt surface (FIG. 8). In FIG. 8, hydrophilicity was evaluated by area of spread and contact angle of 10 µl droplets of distilled water. Note that the contact angle was 0.0±0.0° after UV irradiation on the all titanium surface types tested and titanium alloy surface. Chromium-cobalt alloy also showed an improved hydrophilicity by UV irradiation. Data are shown as the mean±SD (n=3). The symbol "*" indicates that the data are statistical significant between the UV irradiated and non treated control, p<0.0001.

Discussion

The above results show amphiphilic surface of titanium induced by ultraviolet UV light and irradiation results in accelerated and enhanced establishment of bone-titanium implant integration. Generally, successful outcome of implant treatment attributes to generation and preservation of bone around titanium implants, which is referred to as osseointegration or bone-titanium integration. The phenomenon of osseointegration described above is unique in the following ways: (1) De novo bone formation initiates only when implants are placed (see LeGeros R Z, Craig R G, J Bone Miner Res 8 Suppl 2(S583-96 (1993); Ogawa T, Nishimura I, Int J Oral Maxillofac Implants 18(2):200-10 (2003); (2) the bone formation continues for extended period of time even after the healing of the placement site is complete (Grizon F, et al., J Dent 30(5-6):195-203 (2002); Takeshita F, et al., J Biomed Mater Res 37(2):235-42 (1997); (3) once established, the bone mass is sustained without being turned over (Ogawa T, Nishimura I, 2003).

Example 2

Light-Induced Super-Amphiphilic Titanium Accelerates and Enhances Bone-Implant Integration through Selective Cell- and Tissue-Philicity Methods Titanium Samples, Surface Analysis and Ultraviolet UV Light Irradiation.

Two surface types of commercially pure titanium were prepared for cylindrical implants (1 mm in diameter and 2 mm in length) and disks (20 mm in diameter and 1.5 mm in thickness). One had a machined surface, turned by a lathe. The other was dual acid-etched with $H_2SO_4$ and HCl (Osseotite®; Implant Innovations, West Palm Beach, Fla.). The titanium disks were sterilized by gamma radiation. Surface morphology was examined by scanning electron microscopy (SEM) (JSM-5900LV, Joel Ltd, Tokyo, Japan) and atomic force microscopy (SPM-9500J3, Shimadzu, Tokyo, Japan). The average roughness (Ra), root mean square roughness (Rrms) and peak-to-valley (Rp-v) were calculated. Titanium discs and implants were irradiated with 0.1 mW/cm$^2$ UVA and 0.03 mW/cm$^2$ UVB for 48 hours with air ventilation.

Wetability of Titanium Surface.

The contact angle and spread area of distilled water (hydrophilicity test) and glycerol (oleophilicity test). Additionally, blood extracted from rat aorta was used. 10 µL of distilled water and glycerol were gently deposited on the titanium surface and digitally photographed immediately. The spread area was measured as the area of the drop in the top view using a digital analyzer (Image Pro Plus, Media Cybernetics, Silver Spring, Md.). The contact angle θ were obtained by the equation: $\theta = 2 \tan^{-1}(2 h/d)$, where h and d are the height and diameter of the drop in the side view (Oshida, Y., et al., J Mater Science 3, 306-312 (1992)).

Osteoblastic Cell Culture.

Bone marrow cells isolated from the femur of 8-week-old male Sprague-Dawley rats were placed into alpha-modified Eagle's medium supplemented with 15% fetal bovine serum, 50 mg/ml ascorbic acid, $10^{-8}$ M dexamethasone and Antibiotic-antimycotic solution containing 10000 units/ml Penicillin G sodium, 10000 mg/ml Streptomycin sulfate and 25 mg/ml Amphotericin B. Cells were incubated in a humidified atmosphere of 95% air, 5% $CO_2$ at 37° C. At 80% confluency, the cells were detached using 0.25% Trypsin-1 mM EDTA-4Na and seeded onto either the machined titanium or acid-etched titanium disks at a density of 5×10$^4$ cells/cm$^2$ in the above mentioned medium with 10 mM Na-β-glycerophosphate. The culture medium was renewed every three days.

Fibroblastic Culture.

The NIH3T3 fibroblasts were cultured in Dulbecco's Modified Eagle Medium (Gibco BRL, Grand Island, N.Y.), supplemented with 10% Fetal Bovine Serum and 100 U/ml of penicillin, 100 µg/ml of streptomycin and 0.25 µg/ml of amphotericin B. Gingival fibroblasts harvested from the gingival tissue around the lower incisors of 8-week-old Sprague-Dawley rats using a previously established protocol and cultured in the same manner as the NIH3T3 cells.

Proliferation and Chemotaxis Assay.

To examine the cell proliferation, the osteoblastic cells were incubated on the titanium discs horizontally placed on the polystyrene culture dish. The cells were gently rinsed twice with PBS and treated with 0.1% collagenase in 300 μl of 0.25% trypsin-1 mM EDTA-4Na for 15 min at 37° C. A hematocytometer was used to count the number of detached cells. SEM images of the titanium culture were also examined for confirmation. To evaluate the osteoblastic chemotaxis to the titanium surface, the cells were incubated for 3 hours with the titanium discs vertically placed. The attached cells were counted and imaged as described above.

Gene Expression Analysis.

Steady-state gene expression was analyzed using the reverse transcription-polymerase chain reaction (RT-PCR). The primers and conditions for polymerase chain reaction are listed in the Table below.

TABLE

Primers and conditions for polymerase chain reaction

| Target Gene | Forward Primer | Backward Primer | Annealing Temperature | Number of Cycle | Size of PCR Products (bp) |
|---|---|---|---|---|---|
| Collagen I | 5'-GGCAACAGTCGATTCACC-3' | 5'-AGGGCCAATGTCCATTCC-3' | 58 | 28 | 177 |
| Collagen III | 5'-CCTGGACCTCAGGGTATC-3' | 5'-TGCAGGGCCTGGACTACC-3' | 60 | 25 | 498 |
| Osteocalcin | 5'-GTCCCACACAGCAACTCG-3' | 5'-CCAAAGCTGAAGCTGCCG-3' | 61 | 25 | 380 |
| Osteopontin | 5'-GATTATAGTGACACAGAC-3' | 5'-AGCAGGAATACTAACTGC-3' | 45 | 19 | 287 |
| GAPDH | 5'-TGAAGGTCGGTGTCAACGGATTTGGC-3' | 5'-CATGTAGGCCATGAGGTCCACCAC-3' | 67 | 27 | 983 |

Total RNA in the cultures was extracted using TRIzol (Invitrogen, Carlsbad, Calif.) and purification column (RNeasy, Qiagen, Valencia, Calif.). Following DNAse I treatment, reverse transcription of 0.5 μg of total RNA was performed using MMLV reverse transcriptase (Clontech, Carlsbad, Calif.) in the presence of oligo(dT) primer (Clontech, Carlsbad, Calif.). The PCR reaction was performed using Taq DNA polymerase (EX Taq, Takara Bio, Madison, Wis.) to detect alpha-I type I collagen, osteopontin, and osteocalcin mRNA. The primer sequences and PCR conditions are described in Supplementary Methods. Resulting products were visualized on 1.5% agarose gel with ethidium bromide staining. The intensity of bands was quantified under UV light (Eagle Eye II, Strategene, La Jolla, Calif.). The values were normalized with reference to GAPDH mRNA.

Mineralization Assay.

The mineralized cultures were rinsed three times with distilled water and dried over night and photographed. Digital images were processed to subtract background color using digital imaging software (Adobe Photoshop 5.0, Adobe, San Jose, Calif.). The processed images were analyzed by a digitized image analysis system (Image Pro-plus, Media Cybernetics, MD) for the mineral nodule area defined as (white area/total well area)×100(%).

Animal Surgery.

Five 8-week-old male Sprague-Dawley rats were anesthetized with 1-2% isoflurane inhalation. After their legs were shaved and scrubbed with 10% providone-iodine solution, the distal aspects of the femurs were carefully exposed via skin incision and muscle dissection. The flat surfaces of the distal femurs were selected for implant placement. The implant site was prepared 9 mm from the distal edge of the femur by drilling with a 0.8 mm round burr followed by reamers #ISO 090 and 100. Profuse irrigation with sterile isotonic saline solution was used for cooling and cleaning. One untreated cylindrical implant and one UV irradiated implant were placed into the right and left femurs, respectively. Implant stability was confirmed with a passive mechanical fit. Surgical sites were then closed in layers. Muscle and skin were sutured separately with resorbable suture thread. The University of California at Los Angeles (UCLA) Chancellor's Animal Research Committee approved this protocol and all experimentation was performed in accordance with the United States Department of Agriculture (USDA) guidelines of animal research.

Implant Biomechanical Push-in Test.

This method to assess biomechanical strength of bone-implant integration has been described in Ogawa, T. et al. *J Dent Res* 79, 1857-63 (2000). Briefly, femurs containing a cylindrical implant were harvested and embedded immediately in auto-polymerizing resin with the top surface of the implant level. The testing machine (Instron 5544 electromechanical testing system, Instron, Canton, Mass.) equipped with a 2000 N load cell and a pushing rod (diameter=0.8 mm) was used to load the implant vertically downward at a crosshead speed of 1 mm/min. The push-in value was determined by measuring the peak of load-displacement curve.

Histological Preparation.

Five rats were sacrificed at each 2- and 4-week post-operation for the original acid-etched implant and UV-irradiated acid-etched implant groups. The femur was harvested and fixed in 10% buffered formalin for 2 weeks at 4° C. The specimens were dehydrated in an ascending series of alcohol rinses and embedded in light-curing epoxy resin (Technovit 7200 VLC, Hereaus Kulzer, Wehrheim, Germany) without decalcification. The embedded specimens were sawed perpendicular to the longitudinal axis of the cylindrical implants at a site 0.5 mm from the apical end of the implant. The specimens were ground to a thickness of 30 μm with a grinding system (Exakt Apparatebau, Norderstedt, Germany). The sections were stained with Goldner's trichrome stain and observed with a light microscope.

Histolomorphometry.

A 40× magnification lens and 2× zoom on a computer display were used for computer-based histomorphometric measurements (Image Pro-plus, Media Cybernetics, Silver Spring, Md.). To identify the details of the tissue structure, microscopic magnification up to 200× was used. Implant histomorphometry that discriminates the implant-associated bone and non-implant-associated bone was established (Ogawa, T., et al., *J Prosthodont* 11, 241-7 (2002)). Based on the method, the tissue surrounding implants were divided into two zones as follows: Proximate zone, the circumferential zone within 50 μm of the implant surface; distant zone, the circumferential zone from 50 μm to 200 μm of the implant surface. Then, the following variables were analyzed:

Bone-implant contact (%)=(sum of the length of bone-implant contact)/(circumference of the inner chamber)×100, where the implant-bone contact was defined as the interface where bone tissue was located within 20 μm of the implant surface without any intervention of soft tissue;

Bone volume in proximate area (%)=(bone area in proximate zone)/(area of proximate zone)×100; and Bone volume in distant area (%)=(bone area in distant zone)/(area of distant zone)×100.

Statistical Analysis.

T-test was used to examine differences between the untreated control and UV irradiated experimental group; <0.05 was considered statistically significant.

Results

Light-Treatment Creates Amphiphilic Surfaces on Different Titanium Topographies.

Figure 9A:
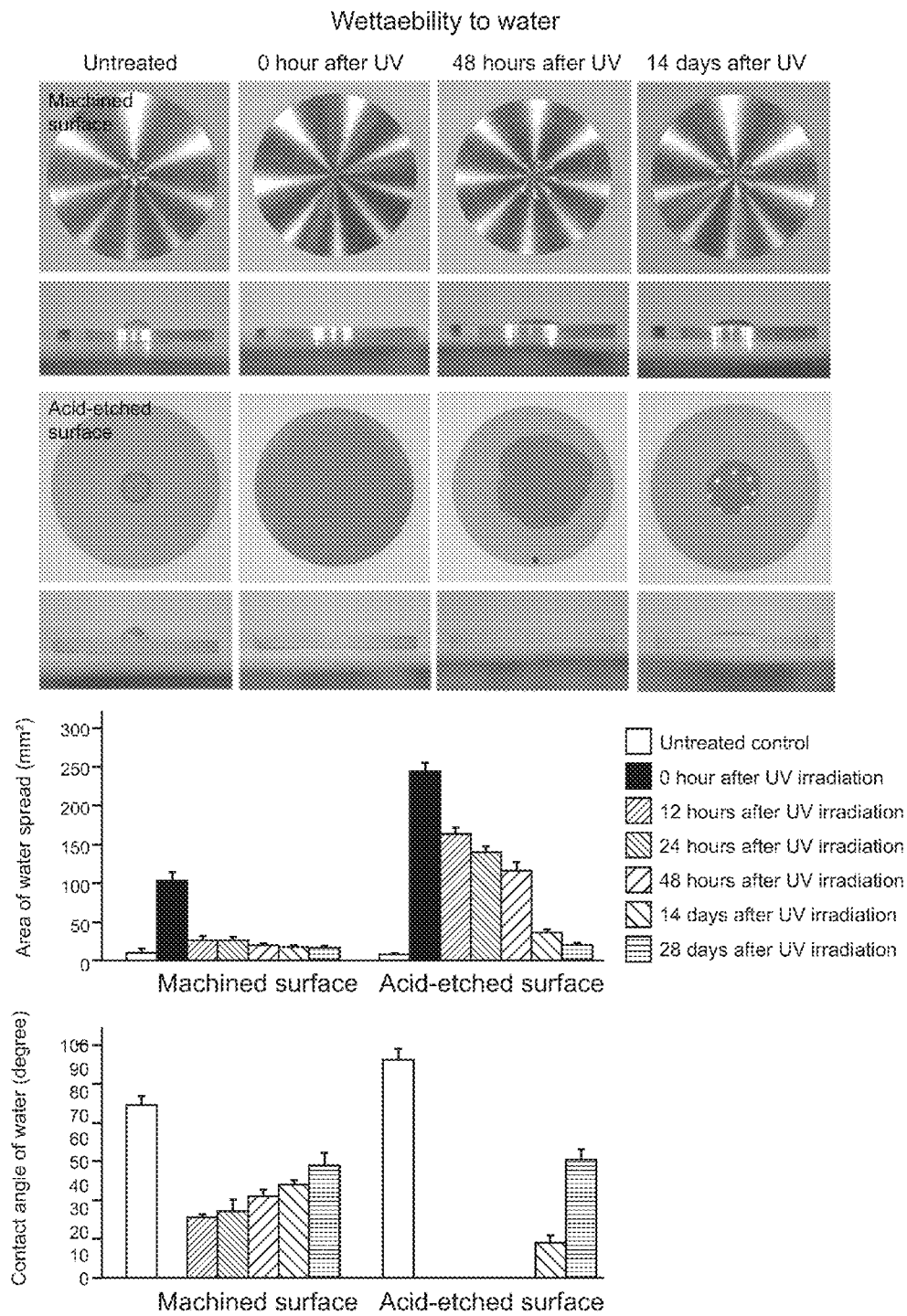
FIGS. 9a-9c show the light-induced changes of wettability of titanium surfaces having two different surface topographies: machined and acid-etched surfaces.

Light-generation of a highly amphiphilic (both hydrophilic and oleolphilic) titanium surface was first introduced in 1997 (Wang, R., et al., Nature 388, 431-432 (1997)). The UV light-inducible changes in wettabilities (hydrophilicity, oleophilicity and hemophilicity) of titanium having different surface topographies and their preservation were examined. Two different surface topographies of titanium were prepared: machined and acid-etched surfaces. Following the light treatment for 48 hours at a level of 0.1 mW/cm$^2$ UVA and 0.03 mW/cm$^2$ UVB, the wettability was evaluated by the spread area and contact angle that liquid drops formed. The spread area of 10 μl water drop dramatically increased after the light treatment for both machined (13 times) and acid-etched surface (30 times) (FIG. 9a). FIG. 9a shows hydrophobic surfaces before the light treatment and highly hydrophilic surfaces after the treatment. As shown in FIG. 9a, preservation and diminution of the light-induced hydrophilicity are demonstrated for the both surface types. The hydrophilicity was evaluated by the spread area (the top views of titanium discs) and the contact angle (the side views of titanium discs) of 10 μl droplets of distilled water. Note that the contact angle is 0.0±0.0° (super-hydrophilic) after the light treatment on the both surface topographies. The contact angle of water before the treatment, which was 69.9° and 88.4° for the machined and acid-etched surface, respectively, plummeted to 0.0±0.0° after the treatment, indicating the emergence of super-hydrophilic surfaces. The light-induced hydrophilicity was diluted as the time passed, and was more effective and sustained for the acid-etched surface than for the machine surface. The hydrophilicity represented by spread area was maintained over 2 times and 13 times for the machined and acid-etched surfaces, respectively, after 48 hours of the treatment. The hydrophilicity, measured by water spread, of the light-treated acid-etched surface was twice as great as the untreated control even after 4 weeks.

Figure 9B:
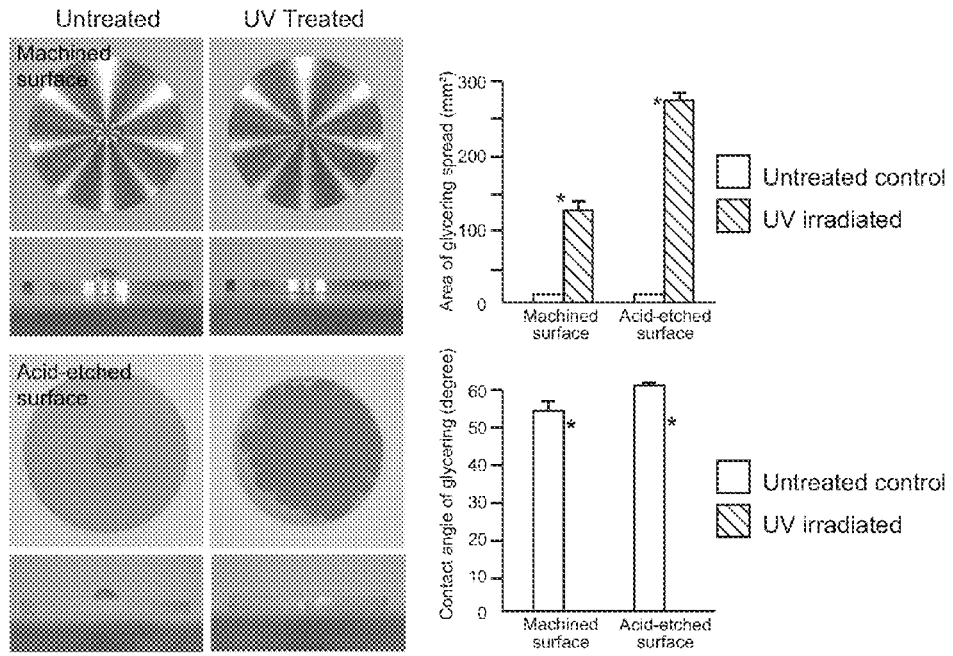
Figure 9C:
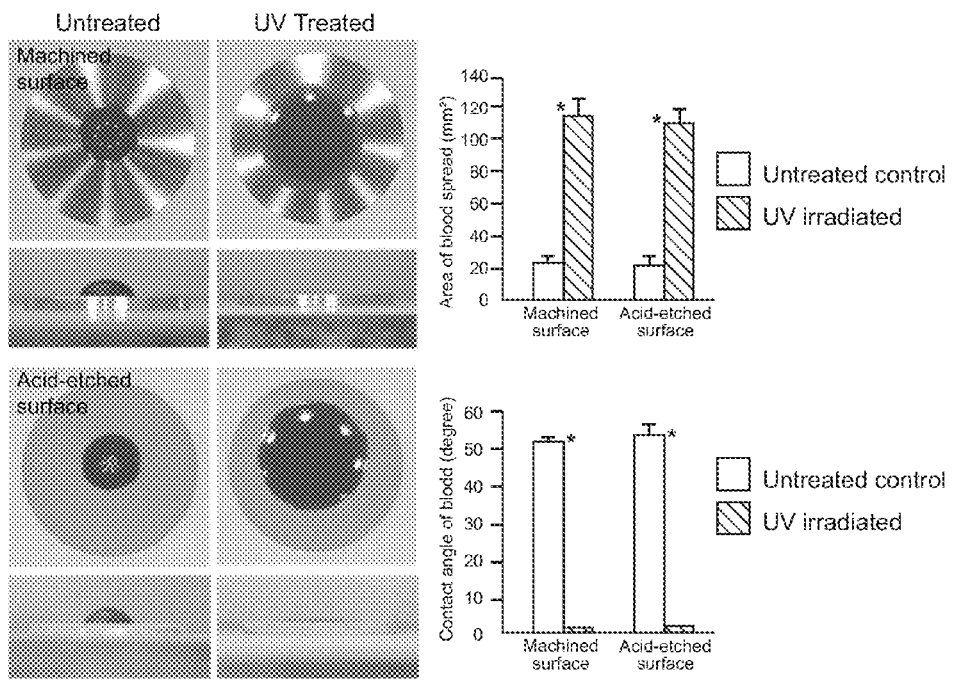

Dramatic gain of oleophilicity was also found using 10 μL drop of glycerol (FIG. 9b) and of hemophilicity using 50 μL drop of blood (FIG. 9c) for both surface types, confirming the establishment of light-generated super-amphiphilic (both hydrophilic and oleophilic) surfaces of titanium having different surface topographies. FIG. 9b shows oleophobic surfaces before light treatment that changed into highly oleophilic surfaces after the treatment, evaluated by 10 μl droplets of glycerol. FIG. 9c shows highly hemophilic surfaces of light-treated titanium surface, evaluated by 50 μl droplets of blood extracted from the rat aorta ("*" indicates that the data indicates that the data are statistically significant between the light treated and untreated titanium disks, p<0.0001).

Figure 10A:
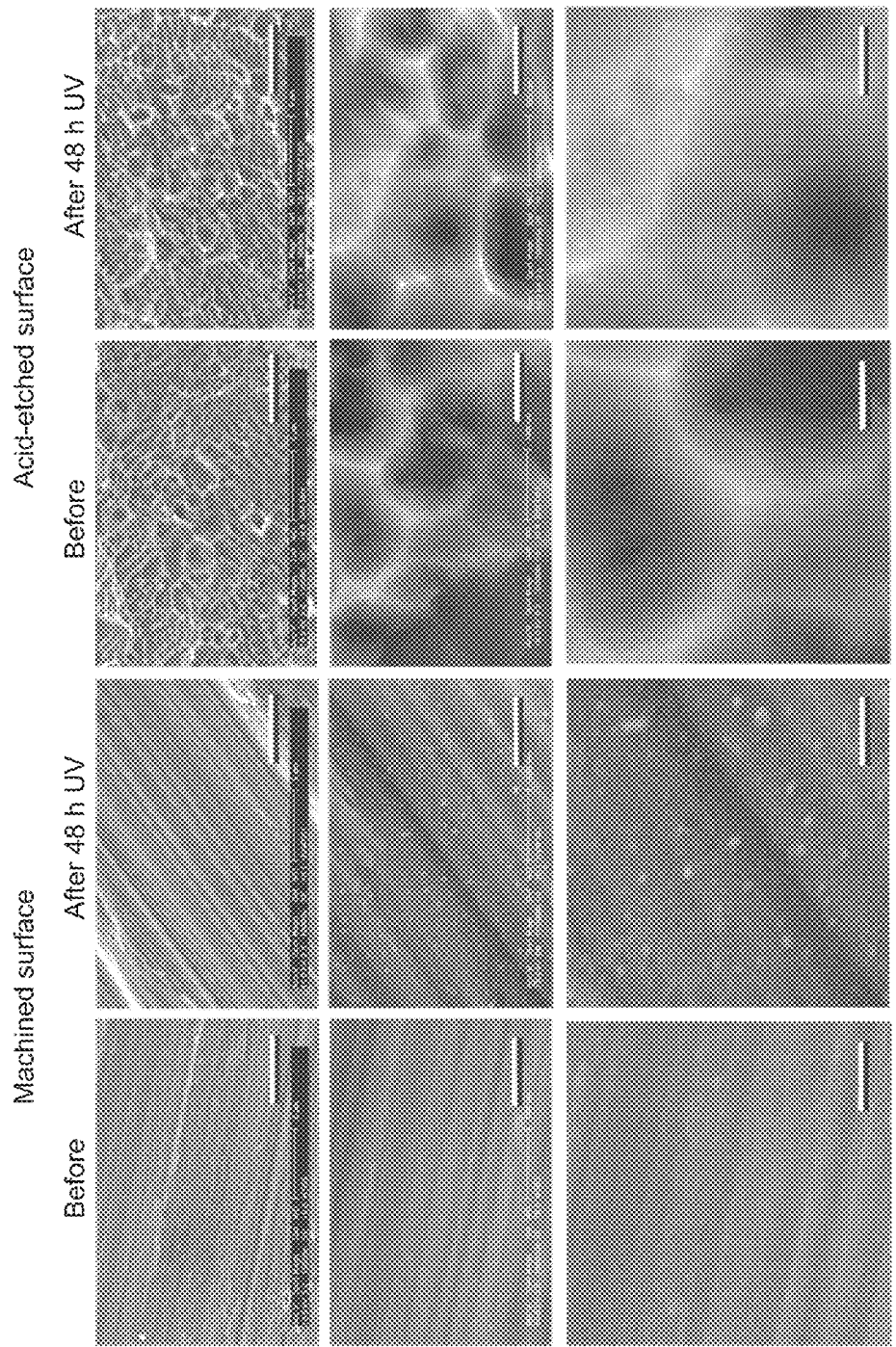

The UV light irradiation described herein alters surface topography of the titanium surfaces. Scanning electron microscopy (SEM) examination showed isotropically and concentrically turned ridges on the machined surface before the light treatment (FIG. 10a), whereas the acid-etched surface was uniformly roughened. High magnification SEM revealed the emergence of nanospheres on the both titanium surfaces after the light treatment. The size of the nanospheres ranged 10-70 nm in diameter. Two-dimensional AFM images also revealed the nanometer-scale changes of contrast on the light-treated surfaces of the machined and acid-etched titanium. FIG. 10a shows the scanning electron micrographs of the machined and acid-etched surfaces before and after the light treatment at a level of 0.1 mW/cm$^2$ UVA and 0.03 mW/cm$^2$ UVB for 48 hours. The circular contrasts ranged 50-600 nm in diameter (FIG. 10b). Both surface types were composed of commercially pure Ti with no contamination as shown by an energy dispersive X-ray (EDX) analysis (FIG. 10c). FIG. 10b shows the atomic force micrographs (AFM) of the machined and acid-etched surfaces before and after the light treatment at a level of 0.1 mW/cm$^2$ UVA and 0.03 mW/cm$^2$ UVB for 48 hours. FIG. 10c showing the energy dispersive spectroscopic elemental spectrums of the machined and acid-etched surfaces before and after the light treatment at a level of 0.1 mW/cm$^2$ UVA and 0.03 mW/cm$^2$ UVB for 48 hours.

Light-Treated Ti Attracts Osteoblasts and Promotes their Proliferation.

Figure 11A:
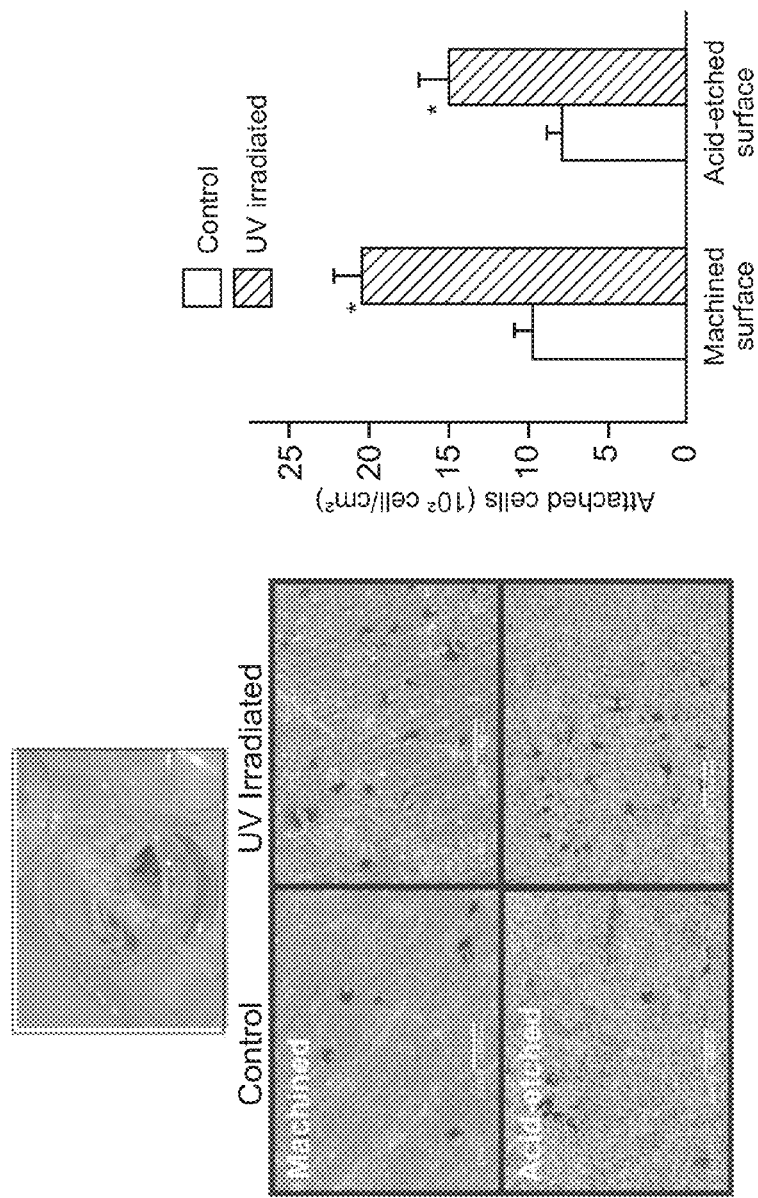
FIGS. 11a-11f demonstrates cell-philicity of titanium surfaces created by the light treatment.
Figure 11B:
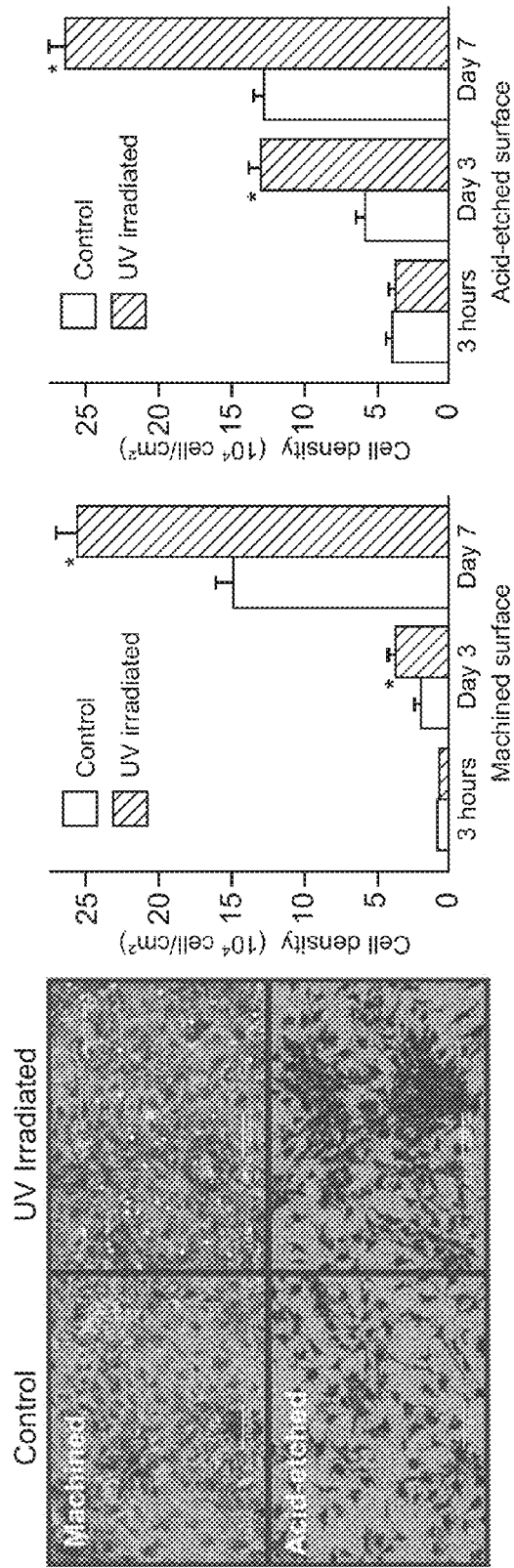

The initial behavior of osteoblasts on light-treated titanium surfaces and tested a hypothesis that light-induced amphiphilicity creates osteoblastophilic environment was investigated. The osteoblastophilicity was examined by chemotaxis and proliferative capability of osteoblasts. To evaluate the chemotaxis to the light-treated titanium, osteoblastic cells derived from rat bone marrow stem cells (BMSCs) were incubated for 3 hours in the polystyrene dish in which titanium discs were placed vertically (FIG. 11a). FIGS. 11a and 11b show that cell attractiveness (FIG. 11a) and cell proliferation (FIG. 11b) were increased by the UV light treatment of the both machined and acid-etched titanium surfaces in vitro culture.

Double the cells were attached to the light-treated machined and acid-etched surfaces than respective untreated surfaces. SEM image of the titanium surfaces confirmed the light-enhanced chemotaxis. To evaluate the cell proliferation, the osteoblastic cells were inoculated onto the machined and acid-etched titanium discs horizontally placed in the polystyrene dish. The light-treatment doubled the proliferation on both surface types (FIG. 11b).

In the test shown in FIG. 11a, the bone marrow stem cell (BMSC)-derived osteoblasts were incubated with titanium plates set up vertically (upper left panel). The attached cells to the titanium plates with or without UV pre-treatment were counted after 3 hours of incubation (right panel). SEM images were taken to confirm the results (left panel). In the test shown in FIG. 11b, the proliferation was evaluated by the cell density at three different time points. The titanium discs with or without the light treatment were placed horizontally in the polystyrene culture dish. The cells were trypsinized and counted using hematocytometer (right panel). Data are shown as the mean±SD (n=3) ("*" indicates that the data are statistically significant between the light treated and untreated control, p<0.0001). SEM images supporting the quantitative results are also presented.

Light Treatment Promotes Osteoblastic Maturation and Mineralization.

Figure 11C:
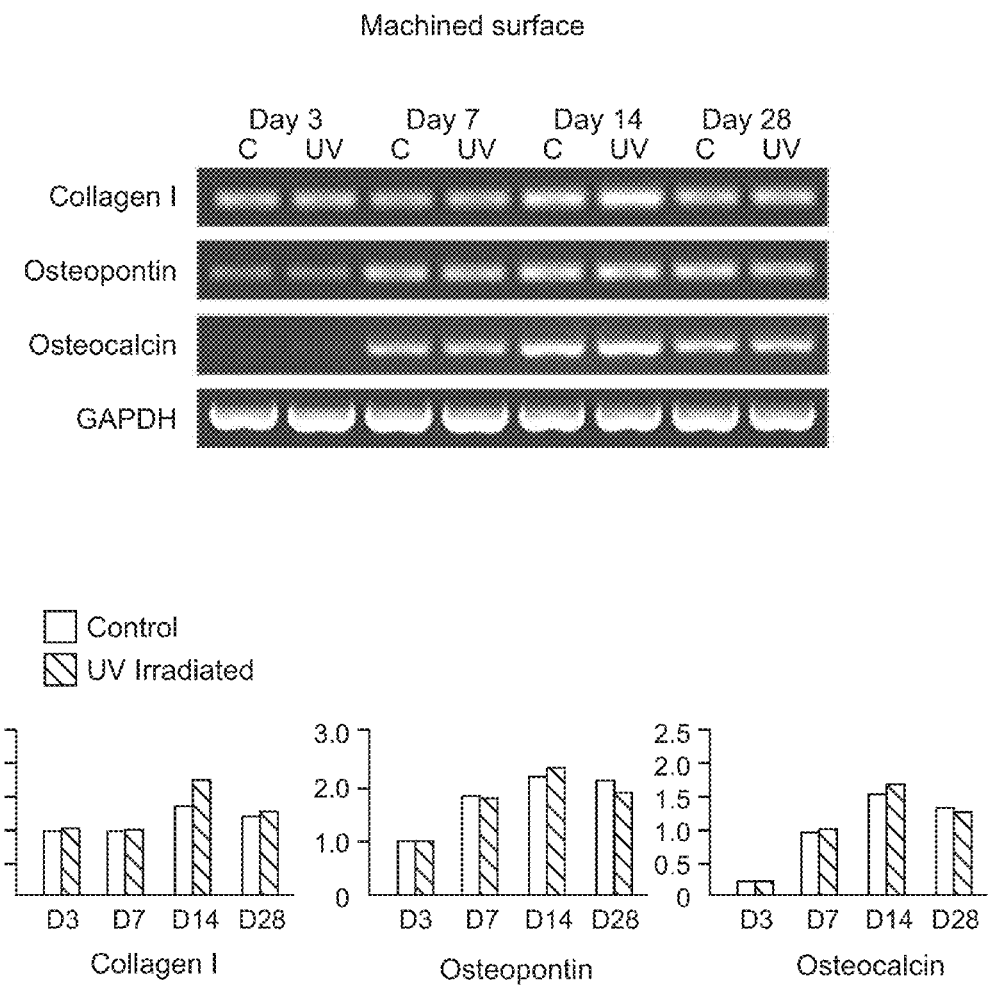
Figure 11C:
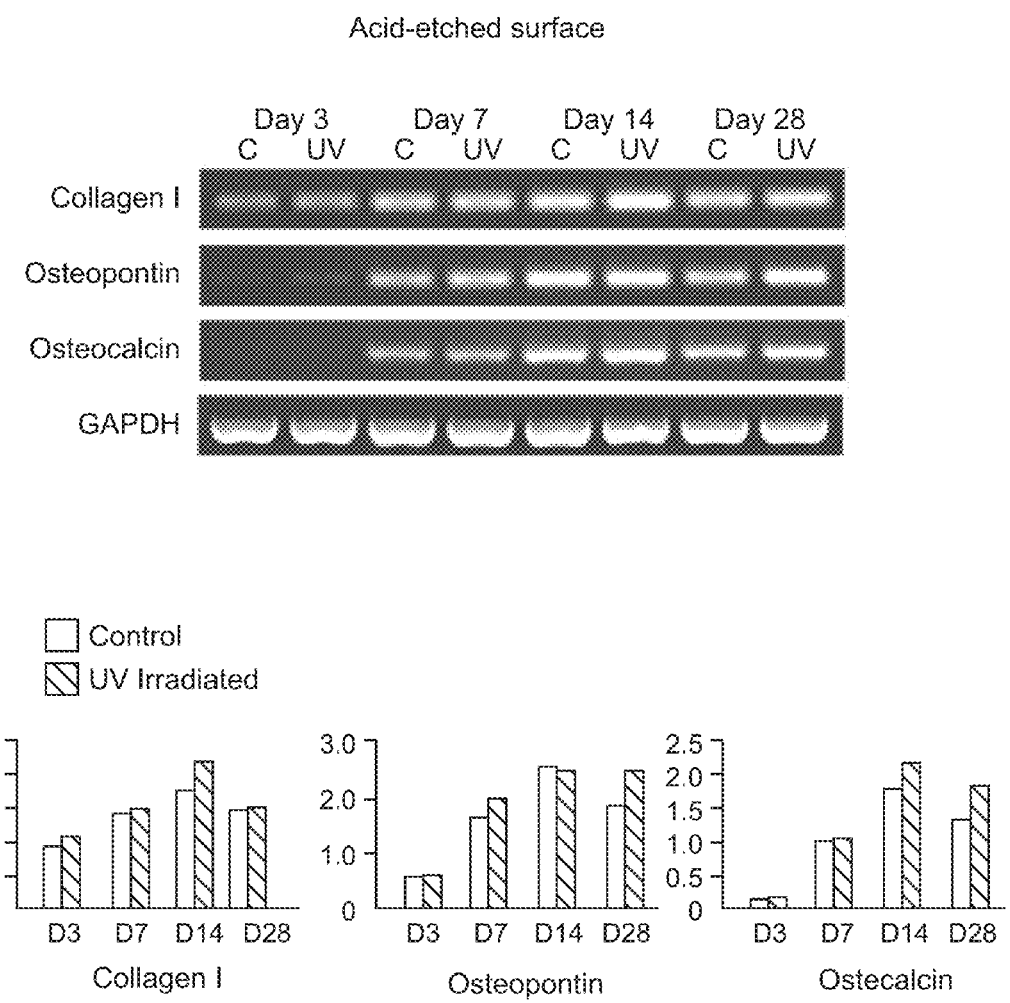

When proliferative activity is dominant, differentiation/maturation activity should be suppressed at the individual cell level in osteoblasts (see, e.g., Stein, G. S. & Lian, J. B., *Endocr Rev* 14, 424-42 (1993); Siddhanti, S. R. & Quarles, L. D., *J Cell Biochem* 55, 310-20 (1994); Alborzi, A., et al., *J Craniofac Genet Dev Biol* 16, 94-106 (1996)); nevertheless the increased cell number provoked on the light activated titanium may facilitate more inter-cellular interaction, leading to a boost of osteoblastic differentiation at the cell population level. To test this theory, the gene expression of the osteoblastic differentiation markers was examined by RT-PCR (reverse transcriptase-polymerase chain reaction) in the bone marrow stem cell (BMSC)-derived osteoblastic cultures on titanium (FIG. 11C). FIG. 11c shows the expression of bone-related genes after the light treatment on titanium. The BMSC-derived osteoblasts were cultured on titanium with or without light treatment, and the steady-state gene expression was assessed using a reverse transcriptase-polymerase chain reaction (RT-PCR). Representative electrophoresis images are shown on top. The quantified expression level and time course of the genes relative to the level of GAPDH mRNA expression are presented in the bottom.

Figure 11D:
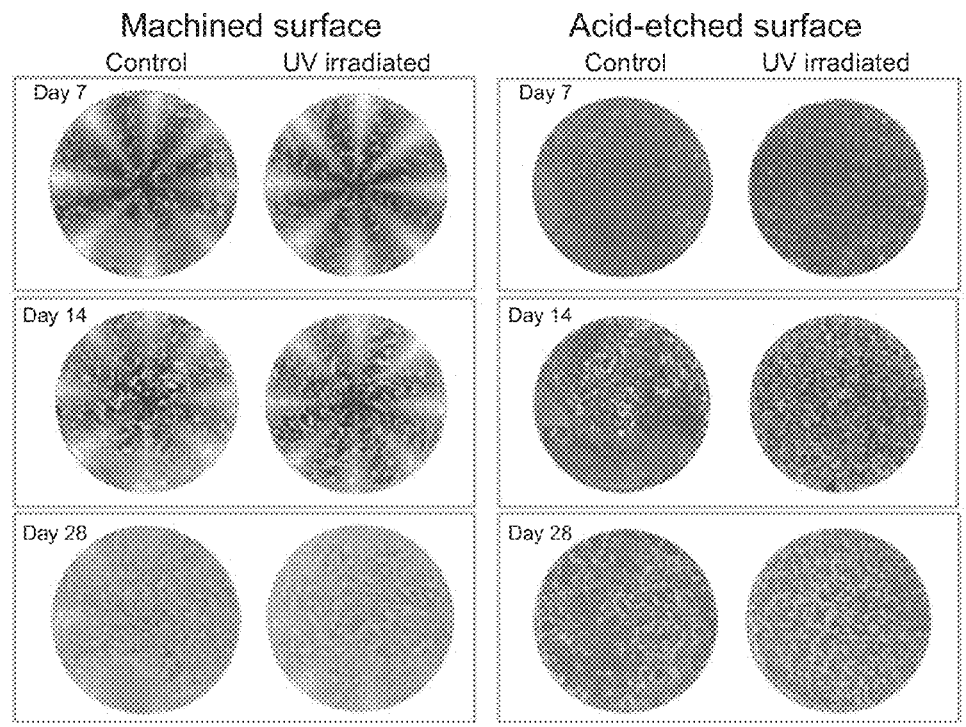
Figure 11D:
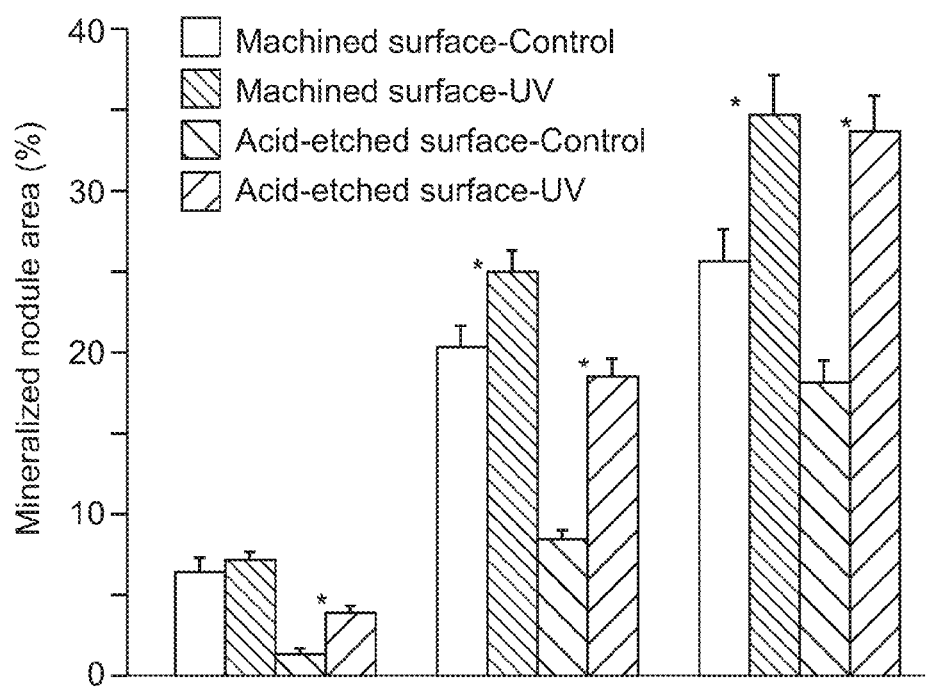

The early stage-expression of the differentiation marker genes (up to day 7) remained the same between the light-treated and untreated surfaces of both machined and acid-etched titanium. At the mid and late stages of culture (day 14 through 28), upregulated expression (over 30% difference) of these marker genes was found on the light-treated titanium of the both surface types, indicating the promoted differentiation and maturation of osteoblasts. The effect of the light-treatment on the osteoblastic mineralizing potential was also evaluated by the formation of mineralizing nodule in the BMSC/osteoblastic cultures (FIG. 11d). The increased area of mineralizing nodule after light-treatment was found on both machined and acid-etched titanium surfaces; the effect was more remarkable for the acid-etched surface showing 100% to 150% increase. FIG. 11d shows the mineralizing capability of osteoblastic cultures by the light treatment on titanium. The left panels show representative images of the mineralized cultures on the machined titanium surface and acid-etched titanium surface with or without the treatment, while the right panel show quantitative mineralized nodule area The percentage of the mineralized nodule area relative to the culture area was measured using a digital image analyzer. Data are shown as the mean±SD (n=3) ("*" indicates that the data are statistically significant between the UV irradiated and non treated control, $p<0.0001$).

Selective Suppression of Fibroblastic Proliferation on Light-Treated Ti.

Figure 11E:
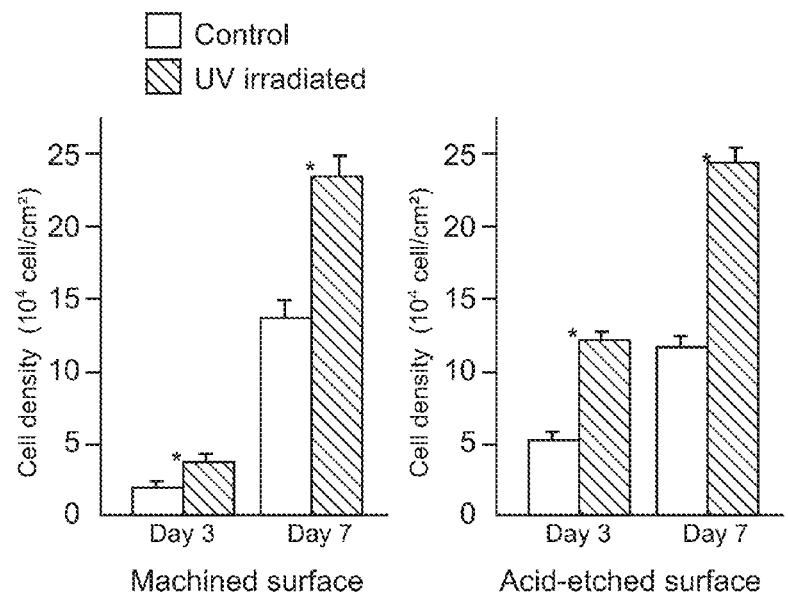
Figure 11F:
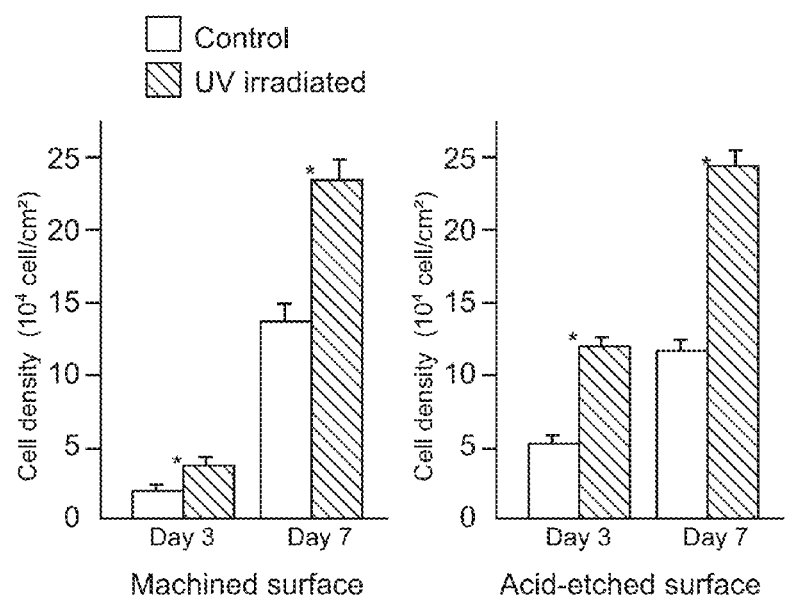

The intervention of connective tissue between newly formed bone and titanium, more or less, is a critical downside phenomenon in accomplishing direct bone contact to titanium. However, the fibroblastic response associated with the process of bone-titanium integration has rarely been studied. The possibility to control fibroblastic growth by the light treatment can be determined by the question of whether the light-treated titanium affects fibroblastic proliferation. Surprisingly, the light treated machined surface and light-treated acid-etched surface induced opposite effects. The proliferation of both NIH3T3 fibroblasts and rat gingival primary fibroblasts was promoted on the light-treated machined surface compared to the untreated machined surface, but suppressed on the light-treated acid-etched surface compared to the untreated acid-etched surface (FIGS. 11e and 11f). Both the machined titanium surface and the acid-etched titanium surface are therefore osteoblastophilic and fibroblastophilic. FIGS. 11e and 11f show that the proliferation of the NIH3T3 fibroblasts (FIG. 11e) and primary gingival fibroblasts (FIG. 11f) were affected by the light treatment differently on the machined and acid-etched surfaces.

In the tests shown in FIGS. 11e and 11f, the fibroblastic proliferation was evaluated using two different cell types: NIH3T3 fibroblasts and rat gingival fibroblasts. Data are shown as the mean±SD (n=3) ("*" indicates that the data are statistically significant between the light-treated and untreated titanium, $p<0.001$).

Light Treatment Accelerates and Enhances Titanium Implant Stabilization.

Figure 12A:
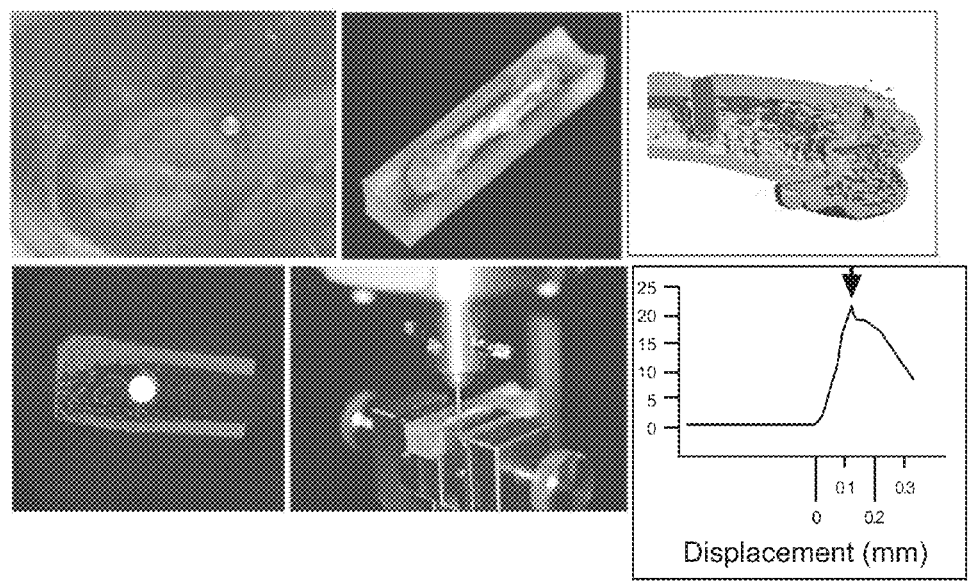
FIGS. 12a and 12b show light enhanced bone-titanium integration evaluated by biomechanical push-in test.

In vivo establishment of implant stability is a most pertinent variable that reflects clinical significance of implants as a load-bearing anchorage. In vivo stability of titanium implants with or without light treatment was examined using the established biomechanical implant push-in test in the rat model (Ogawa, T. et al. *J Dent Res* 79, 1857-63 (2000)) (FIG. 12a). In the test shown by FIG. 12a, titanium implants with or without UV light pre-treatment were placed into the rat femur, and the femur specimen with the implants were harvested and embedded into the metheylmethacrylate block. The microCT was used to confirm the implants were free from cortical bone support from the lateral and bottom sides of the implant. Biomechanical stability of the implants was then evaluated at 2 and 4 weeks post-implantation by measuring the breakage strength against push-in load.

Figure 12B:
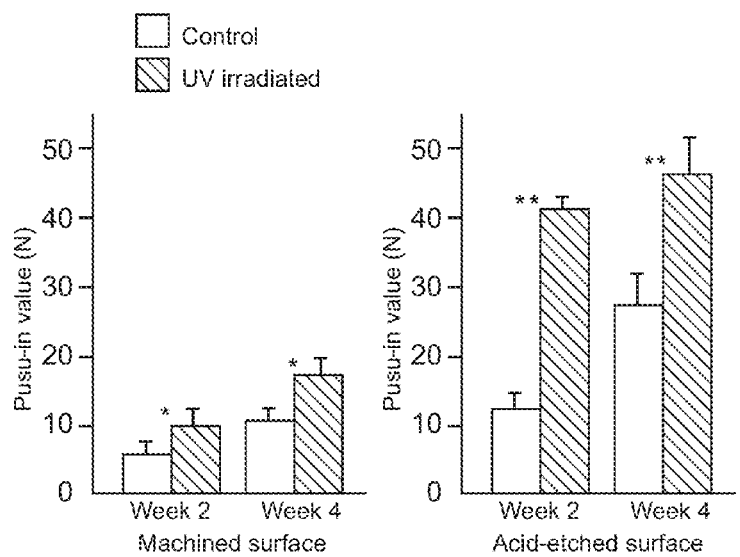

Implants were placed into the rat femur at 9 mm from the knee end, and the position of the implant was confirmed not to be involved in the growth plate or the lateral and bottom cortical bony support. The implants, while being pushed-in vertically, gave a mechanically predicted load-displacement curve, and the force at a point of breakage (maximum force on the load-displacement curves) was measured as a push-in value. The push-in value at 2 weeks post-implantation soared 1.8 times and 3.1 times, respectively, for the machined surface and the acid-etched surface by the light treatment (FIG. 12b). At week 4, the push-in value of the light-treated implants maintained the superiority over the untreated implants by 50% and 60%, respectively, for the machined surface and the acid-etched surface. FIG. 12b shows the push-in value of the machined and acid-etched implants with or without the light treatment. Data are shown as the mean±SD (n=5) (statistically significant between the light treated and untreated implants, "**" indicating $p<0.001$; "*" indicating $p<0.001$).

Optimized Bone-Titanium Integration by Light Treatment.

The increased biomechanical fixation of the light-treated titanium implants can be due to the increased bone volume around implants, increased bone-to-implant contact, or combination of both. Also, whether the demonstrated fibroblastoohobicity of the light-treated acid-etched surface leads to soft (connective) tissue-phobicity can also be important. To address these, histological and histomorphometric analyses of bone and soft tissue formation around implants were undertaken. Given the advantages in the biomechanical fixation of the acid-etched surface over the machined surface, as well as the newly-found fibroblastophobicity, the ached-etched surface was selected to explore such potential effects of the light-treatment. Cylindrical acid-etched implants with or without light treatment were placed into the rat femur, and the non-decalcified cross-sections, perpendicular to the long axis of the implant, were processed for Goldner's trichrome histology.

Figures 13A, 13B, 13C, 13D:
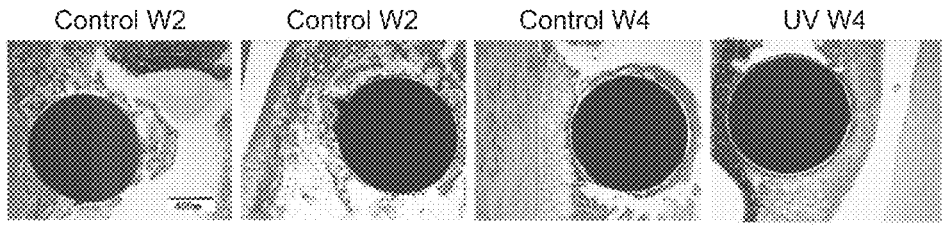
FIGS. 13a-13p show the effect of light-treated acid-etched titanium on peri-implant bone generation.
Figures 13E, 13F, 13G, 13H:
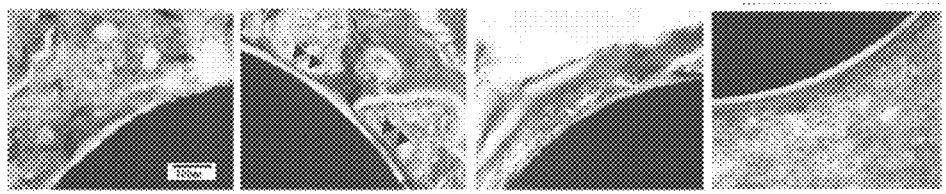
Figures 13I, 13J, 13K, 13L:
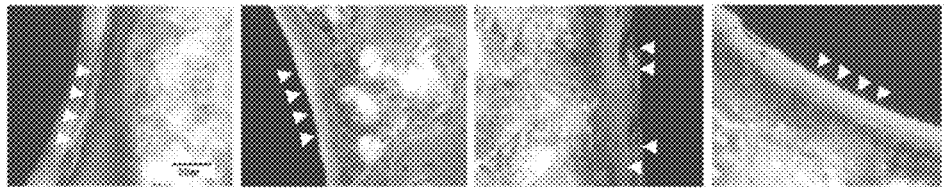
Figure 13M:
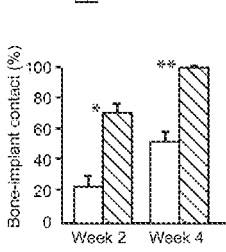
Figure 13N:
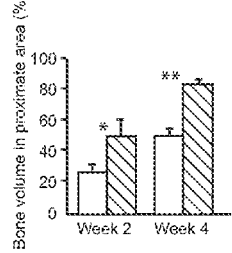
Figure 13O:
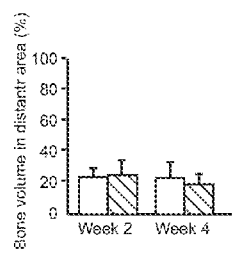
Figure 13P:
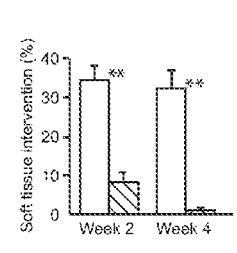

FIGS. 13a-13p present some of the results of the test. Representative histologic sections of the acid-etched titanium implants with Goldner's trichrome stain were shown in an original magnification of ×40 for panels a-d (FIGS. 13a-13d), ×40 for panels e-h (FIGS. 13e-13h), and ×100 for panels i-l (FIGS. 13i-13l). Note that, at week 2, the light-treated implant is associated with vigorous bone taxis that prevents soft tissue from intervening between the bone and implants (arrow heads in FIG. 13f), leading to direct bone deposition onto the implant surface at week 4 (arrow heads in FIG. 13j). In contrast, the bone around the untreated control extends less and involves soft tissue that migrated into the bone and implant surface, interfering the establishment of direct bone-implant contact (arrow heads in FIG. 13i). Such differences in the implant interfacial bone morphogenesis are clearly seen in week 4 sections (FIGS. 13g and 13h). The extensive bone generation without soft tissue interposition (arrow heads) is indicated around the light-treated implants (l) (FIG. 13l), while the bone around the untreated implants is largely kept apart from the implant surface by soft tissue (k) (FIG. 13k). The average histomorphometric values with standard deviation (error bars) of bone-implant contact (m) is shown in FIG. 13m, while FIG. 13n shows the bone volume in proximate zone (n), FIG. 13o shows the bone volume in distant zone (o), and FIG. 13p shows the soft tissue-implant contact (p). The statistically significant between the light-treated and untreated implants is indicated by the symbols "*" or "**" (*$p<0.001$; **$p<0.0001$).

At week 2, bone tissue or bonelike tissue with a woven, immature appearance formed in the area relatively distant from the implant surfaces for both the control acid-etched implants and light-treated acid-etched implant (FIGS. 13a and 13b). A focus on the adjacent area to the implant surface revealed the evident differences in bone growth between the light-treated and untreated implants in which bone around the light-treated implant migrated more extensively onto the implant surface than that around the untreated control (FIGS. 13a and 13b). The continuity of bone tissue resulting from the well-spread de novo bone fragments is seen along the light-treated implant. The high magnification images clearly illustrated the enhanced bone growth extending along the light-treated surface (FIGS. 13e and 13f), and revealed another notable difference regarding soft tissue intervention. Some bone tissue around the untreated control implants was associated with soft tissue interposed between the bone and implant (FIG. 13i), which was rarely observed around the light-treated implant, allowing the de novo bone tissue directly contact to the implant surface (FIG. 13j).

At week 4 the trabecular structure of bone tissue dramatically decreased, and the bone tissue with the lamellar structure extensively encapsulated implants (FIGS. 13c and 13d). Such advancement of bony remodeling was more prominent around the light-treated surface. The control implants still exhibited fibrous connective tissue intervening between the bone and implant surface (FIGS. 13c, 13g and 13k), while the implants with the light-treatment were nearly entirely surrounded with bone directly deposited onto the titanium surfaces without connective tissue intervention (FIGS. 13d, 13h and 13i).

Bone histomorphometry showed that the percentage of bone-implant contact for the light-treated implants was consistently greater than for the control implants (approximately 3.0 times at week 2 and 2.0 time at week 4) (FIG. 13m). To discriminately evaluate bone-implant integration from the surrounding bone generation and remodeling, bone volume were measured in two different areas; proximate and distant areas to the implant surface. The areas were segmented based on a previous study describing the bone generation dynamics around implants (Ogawa, T., et al., *J Prosthodont* 11, 241-7 (2002)). The proximate area was defined as the circumferential area within 50 µm of the implant surface, while the distant area as a circumferential area from 50 µm to 200 µm. The bone volume in the proximate area was consistently greater at weeks 2 and 4 for the light-treated implants than for the control implants (FIG. 13n). In contrast, light-induced changes in the bone volume in the distant area were not found (FIG. 13o). There was significant reduction in the percentage of soft tissue-implant contact by the light-treatment (FIG. 13p). The light-treatment for the acid-etched surfaces nearly completely shut out the soft-tissue from between bone and the implant surfaces, particularly at week 4, while over 30% in area of the untreated surface was in contact with soft-tissue at both weeks 2 and 4.

Example 3

Light-Induced Osteoblastophilic Surface Created on Freshly Prepared Sandblasted Titanium Introduction One of the challenges in the development of new titanium implants is how to overcome an inverted correlation between proliferation and differentiation rates of osteoblasts (Stein, G. S. & Lian, J. B. *Endocr Rev* 14, 424-42 (1993); Siddhanti, S. R. & Quarles, L. D., *J Cell Biochem* 55, 310-20 (1994); Alborzi, A., et al., *J Craniofac Genet Dev Biol* 16, 94-106 (1996)). For instance, increased rate differentiation concomitant with diminished proliferation of osteoblasts has been demonstrated in various roughed surfaces, which are common implant surfaces for dental implants (Takeuchi, K., et al., *J Biomed Mater Res A* 72A, 296-305 (2005); Bachle, M. & Kohal, R J., *Clin Oral Implants Res* 15, 683-92 (2004)). Examples 1 and 2 establish that the light-induced super-amphiphilic (hydrophilic and oleophilic) surfaces of titanium that overcomes the osteoblastic nature. The osteoblastic proliferation was increased more than double on the light-treated machined and acid-etched surfaces compared to the untreated ones, while maintaining or increasing the differentiation rate. Then, the phenomenon raised a question of whether the generation of amphiphilicity was due to the removal of the surface contaminants by light-excited hydroxyl groups (hydroxyl radicals) on the titanium surface in that titanium absorbs the organic impurities over time, such as carbon and hydrocarbons, from the atmosphere, water and cleaning liquid. If so, the question becomes one of whether the hydrophilicity acquired on the fresh, bare titanium surfaces cannot be enhanced to a higher degree by light treatment in that the freshly prepared surfaces should contain minimum amount of the surface impurities and hydroxyl groups. If any of the two assumptions are found to be negative, there may be other mechanisms other than the exited hydroxyl-driven surface decontamination, underlying the light-induced super-hydrophilicity that leads to increased osteoblastic proliferation.

Materials and Methods

Titanium Samples, Surface Analysis and Ultraviolet UV Light Treatment.

Disks (20 mm in diameter and 1.5 mm in thickness) made of commercially pure titanium (Grade 2) with machined surfaces were sandblasted with 50 µm aluminum oxide particles at a distance of 1 cm with a pressure of 3 kg/m. Some sandblasted disks were treated with ultra-violet UV light of 0.1 mW/cm2 UVA and 0.03 mW/cm2 UVB for 48 hours under the atmosphere.

Hydrophilicity and Oleophilicity of Titanium Surface.

One (1), five (5) or ten (10) µl of distilled water and 5 µl of glycerol were gently placed on the titanium surface without physical contact and digitally photographed immediately. The spread area was measured as the area of the drop in the top view using a digital analyzer (Image Pro Plus, Media Cybernetics, Silver Spring, Md.). The contact angle θ were obtained by the equation: $\theta = 2\tan^{-1}(2h/d)$, where h and d are the height and diameter of the drop in the side view (Oshida, Y., et al., *J Mater Science* 3, 306-312 (1992)).

Osteoblastic Cell Culture.

Bone marrow cells isolated from the femur of 8-week-old male Sprague-Dawley rats were placed into alpha-modified Eagle's medium supplemented with 15% fetal bovine serum, 50 mg/ml ascorbic acid, $10^{-8}$M dexamethasone, 10 mM Na-β-glycerophosphate and Antibiotic-antimycotic solution containing 10000 units/ml Penicillin G sodium, 10000 mg/ml Streptomycin sulfate and 25 mg/ml Amphotericin B. Cells were incubated in a humidified atmosphere of 95% air, 5% $CO_2$ at 37° C. At 80% confluency, the cells were detached using 0.25% Trypsin-1 mM EDTA-4Na and seeded onto the titanium disks at a density of $5 \times 10^4$ cells/cm$^2$. The culture medium was renewed every three days.

Proliferation Assay.

To examine the cell proliferation, the cells were gently rinsed twice with PBS and treated with 0.1% collagenase in 300 µl of 0.25% trypsin-1 mM EDTA-4Na for 15 min at 37° C. A hematocytometer was used to count the number of detached cells.

Gene Expression Analysis.

To examine the degree of the osteoblastic differentiation, gene expression was analyzed using the reverse transcription-polymerase chain reaction (RT-PCR). Total RNA in the cultures was extracted using TRIzol (Invitrogen, Carlsbad, Calif.) and purification column (RNeasy, Qiagen, Valencia, Calif.). Following DNAse I treatment, reverse transcription of 0.5 µg of total RNA was performed using MMLV reverse transcriptase (Clontech, Carlsbad, Calif.) in the presence of oligo(dT) primer (Clontech, Carlsbad, Calif.). The PCR reaction was performed using Taq DNA polymerase (EX Taq, Takara Bio, Madison, Wis.) to detect alpha-I type I collagen and osteocalcin mRNA. Resulting products were visualized on 1.5% agarose gel with ethidium bromide staining. The intensity of bands was quantified under UV light (Eagle Eye II, Strategene, La Jolla, Calif.). The values were normalized with reference to GAPDH.

Statistical Analysis.

T-test was used to examine differences between the untreated control and light-treated experimental group; <0.05 was considered statistically significant.

Results

Enhanced Amphiphilicity by Light Treatment.

Figure 14A:
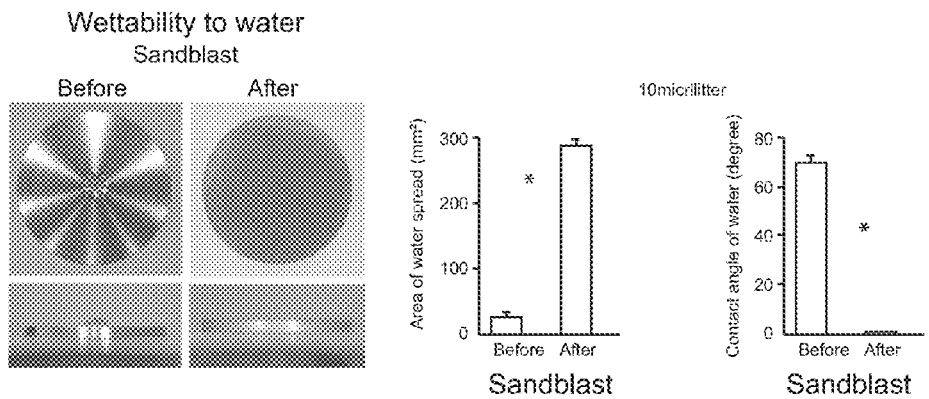
FIGS. 14a-14c show light-induced changes of wettability of sandblasted titanium surfaces.

Sandblasting on the machined surface changed the wettability behavior from hydrophobic to hydrophilic (FIG. 14*a*). The spread area of 10 µl water drop increased 13 times after sandblasting of the machined surface. The contact angle of water before sandblasting, which was 69.9°, plummeted to 2.0° after sandblasting, indicating the generation of super-hydrophilic surfaces. FIG. 14*a* shows hydrophobic machined surfaces and hydrophilic surfaces after sandblasting. The hydrophilicity was evaluated by the spread area (the top views of titanium discs) and the contact angle (the side views of titanium discs) of 10 µl droplets of distilled water.

Figure 14B:
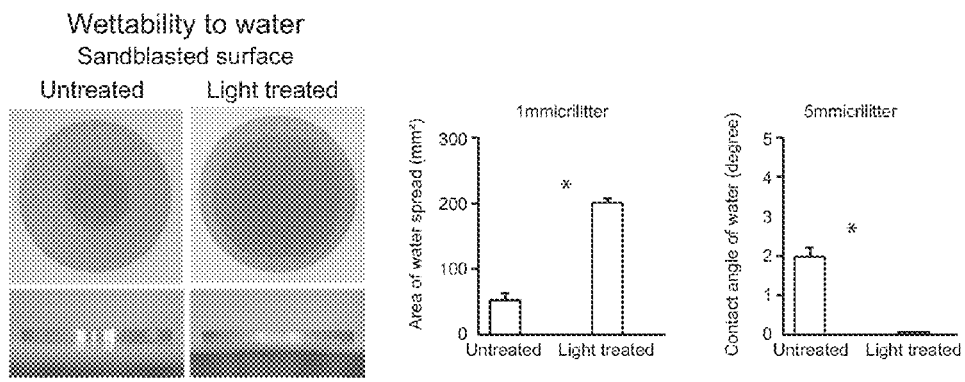

The sandblast-induced super-hydrophilicity was enhanced by the light treatment (FIG. 14*b*). The spread area of 1 µl water drop was 3 times on the light-treated sandblasted surface compared the untreated fresh sandblasted surface. FIG. 14*b* shows the hydrophilicity of the freshly prepared sandblasted titanium surface with or without light-treatment. The spread area of 1 µl droplets of distilled water was greater on the light-treated surface. Note that the contact angle measured using 5 µl water is 0.0±0.0° (super-hydrophilic) after the light treatment.

Figure 14C:
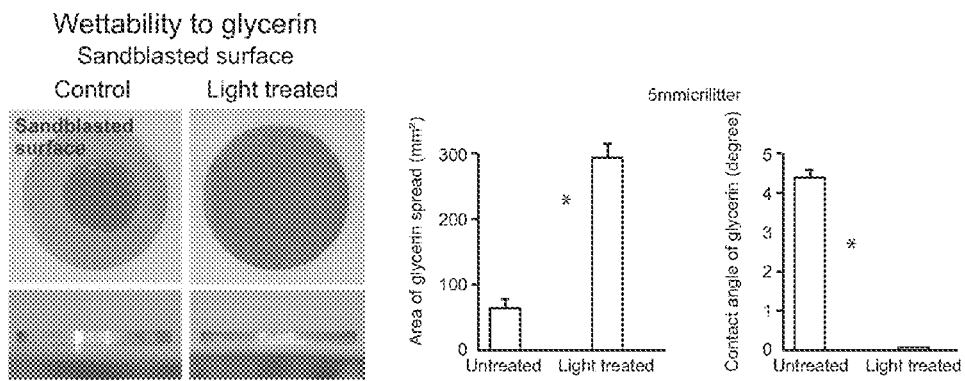

The contact angle measured with 5 µl water drop was 0° when treated with the light. Similarly, super-oleophilicity was further enhanced by the light treatment (FIG. 14*c*), with the spread area of the 5 µl glycerol increased by 4 times. The contact angle of the glycerol on the light-treated surface was 0°, while the one on the untreated surface was 4.3°. FIG. 14*c* shows oleophilicity before the light treatment was enhanced after the light treatment, evaluated by 5 µl droplets of glycerol ("*" indicates that the data are statistically significant between the two groups, p<0.0001).

Light Treated Sandblasted Surface Promotes Osteoblastic Proliferation.

Figure 15A:
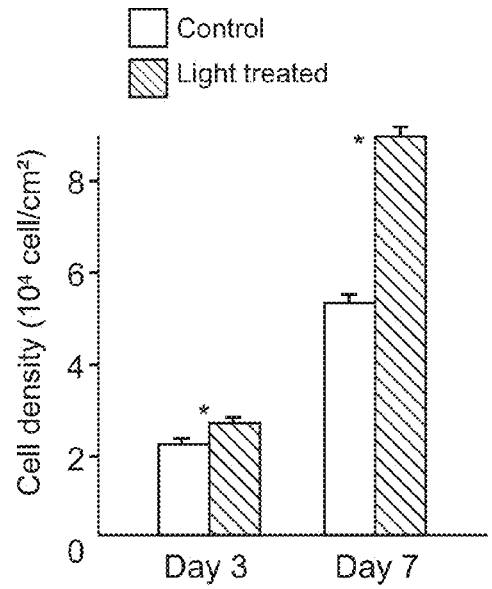
FIGS. 15a and 15b show osteoblastophilic sandblasted surfaces created by light treatment.
Figure 15B:
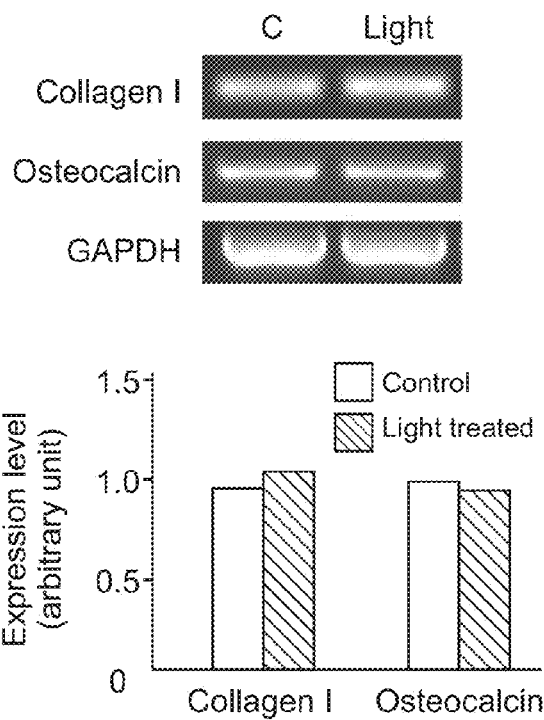

The osteoblasts derived from the bone marrow proliferated more on the light-treated sandblasted surface than on the untreated sandblasted surface (FIG. 15*a*). The cell number at day 7 was increased by 60% by the light treatment. In FIG. 15*a*, the proliferation was evaluated by the cell density at two different time points. Data are shown as the mean±SD (n=3) ("*" indicates that the data are statistically significant between the light treated surface and untreated control, p<0.0001). FIG. 15*b* shows expression of bone-related genes after the light treatment. The BMSC-derived osteoblasts were cultured on the freshly prepared sandblasted surfaces with or without light treatment, and the gene expression was assessed using a reverse transcriptase-polymerase chain reaction (RT-PCR). Representative electrophoresis images are shown on top. The quantified expression level and time course of the genes relative to the level of GAPDH mRNA expression are presented at the bottom.

Light Treatment Maintains Osteoblastic Maturation Capability.

The gene expression of collagen I, a marker of the early osteoblastic differentiation, remained the same level after the light-treatment of the sandblasted surface. The osteocalcin, the late stage marker, was also expressed similarly between the light-treated and untreated surfaces, indicating that the light treatment maintains the osteoblastic maturation capability while increasing the proliferation capability.

Discussions

The study described in this example is demonstrates the possibility of creating light-enhanced hydrophilic surface on the freshly prepared sandblasted titanium and the generation of osteoblastophilicity, i.e., capability to increase the osteoblastic proliferative activity, along with the maintained or increased differentiation activity. The results show that light treatment on the freshly prepared sandblasted surface further enhances the existing hydrophilicity and increases osteoblastophilicity. Therefore, hydration and hydroxylation of the titanium surface are not a necessary process to create the hydrophilic and osteoblastophilic titanium surface.

Example 4

Formation of Bone Cement-Philic Titanium Surface

Introduction

Acrylic resin-based bone cements, primarily having a solid part of a pre-polymerized poly(methyl methacrylate) (PMMA) and a liquid part of methyl methacrylate (MMA), are the most frequently used materials for stabilization and retention of the orthopedic implants. To modify the mechanical properties of the bone cement, various modification techniques have been attempted. The cement containing PMMA fibers in its PMMA matrix seems to increase fracture resistance (Gilbert J L, et al., Biomaterials 1995; 16:1043-55; Wright D D, et a., J Biomed Mater Res 1997; 36:441-53). Addition of bio-glass or bio-ceramic to resin-based cements helps increase the mechanical strength of the PMMA cements (Kobayashi M, et al., J Biomed Mater Res 1999; 46:447-57; Shinzato S, et al., J Biomed Mater Res 2000; 51:258-72). These modifications, however, alter the chemical properties, as well as the mechanical properties, of the materials and require additional characterization of their biological compatibility. Moreover, while these approaches may enhance the intrinsic mechanical properties of the bone cement, they may be less effective in reinforcing the cement-metal interface; debonding of the cement-metallic implant interface has been implicated as a major site of failure initiation (Jasty M, et al., J Bone Joint Surg Br 1991; 73:551-8; Verdonschot N, et al., J Biomech 1997; 30:795-802).

One improvement to the cement-metal interfacial strength is a precoat of bone cement around implants. This process enables a pore-free, uniform coverage of industrial-grade bone cement on the surface of the implant and has been demonstrated clinically successful (Clohisy J C, et al., J Bone Joint Surg Am 1999; 81:247-55; Oishi C S, et al., J Bone Joint Surg Am 1994; 76:1130-6). However, the method does not allow for the hybrid use of implant fixation by bone cement and bone-titanium integration.

Light-generation of an amphiphilic (both hydrophilic and oleolphilic) titanium surface was first introduced in 1997 (Wang R, et al, Nature 1997; 388:431-432). The character of this surface is ascribed to the microstructured composition of hydrophilic and oleolphilic phases, produced by ultraviolet UV light treatment. The possible explanation is, first, that the generation of amphiphilicity was due to the removal of the surface contaminants by light-excited hydroxyl groups (hydroxyl radicals) on the titanium surface. Titanium absorbs the organic impurities over time, such as carbon and hydrocarbons, from the atmosphere, water and cleaning liquid. Second, the light treatment may create surface oxygen vacancies at bridging sites, resulting in the conversion of relevant $Ti^{4+}$ sites to $Ti^{3+}$ sites which are favorable for dissociative water adsorption.

Summary

Described herein is a method for enhancing bone cement-titanium interfacial strength without modifying bone cement materials. The light-inducible changes in wettabilities (hydrophilicity, oleophilicity and hemophilicity) of titanium for bone cement-philicity were examined. The UV light-treated titanium has shown higher bone cement wettability and stronger bone cement-titanium interfacial strength. The effect of the light treatment was proved for different titanium surface topographies of machined, relatively smooth surface and acid-etched, relatively rough surface.

Methods

Titanium Samples, Surface Analysis and Ultraviolet UV Light Treatment.

Two surface types of commercially pure titanium were prepared for cylindrical implants (1 mm in diameter and 2 mm in length) and disks (20 mm in diameter and 1.5 mm in thickness). One had a machined surface, turned by a lathe, and the other was acid-etched with $H_2SO_4$ and HCl. The titanium disks were sterilized by gamma radiation. Titanium discs and implants were treated with 0.1 mW/cm2 UVA and 0.03 mW/cm2 UVB for 48 hours with air ventilation. The surfaces of the titanium samples with or without the light treatment were examined by scanning electron microscopy (SEM) (JSM-5900LV, Joel Ltd, Tokyo, Japan), an energy dispersive X-ray spectrometer (EDX) (JSM-5900LV, Joel Ltd, Tokyo, Japan) and atomic force microscopy (SPM-9500J3, Shimadzu, Tokyo, Japan).

Hydrophilicity and Bone Cement-Philicity of Titanium Surface.

The contact angle and spread area of distilled water (hydrophilicity test) and bone cement (bone cement-philicity test) were evaluated. Ten (10) µl of distilled water was gently placed on the titanium surface and digitally photographed immediately. The spread area was measured as the area of the drop in the top view using a digital analyzer (Image Pro Plus, Media Cybernetics, Silver Spring, Md.). The contact angle θ were obtained by the equation: $\theta=2\tan^{-1}(2h/d)$, where h and d are the height and diameter of the drop in the side view (Oshida Y, et a., J Mater Science 1992; 3:306-312). Bone cement was prepared by mixing the 18.88 g liquid and 20 g powder for ten seconds, which was double liquid ratio of the manufacture's instruction Endurance MV, DePuy Orthopaedics, Warsaw, Ind.). Ten (10) µl of the mixed cement was gently placed on the titanium surface.

Implant Mechanical Push-Out Test.

This method was originally developed and established to assess biomechanical strength of bone-implant integration, and the detail has been described elsewhere (Ogawa T, et al., J Dent Res 2000; 79:1857-63). This method was used herein to assess the implant-bone cement interfacial strength. The cylindrical implants (1 mm in diameter and 2 mm in length) with or without the light treatment were placed into the acrylic block made of heat-cure hard metheylmethacrylate resin (FIG. 16a). The acrylic block had pre-made holes of 2 mm in diameter and of 2 mm in height (FIG. 16b). The bone cement was prepared by mixing the powder and liquid as instructed by the manufactures (10 second mixing of 18.88 g liquid and 40 g powder), and the implants pasted with the prepared bone cement were placed into the holes with the implant top surface level and flushed with the resin block top surface. The bone cement was polymerized in a 37° C. for 24 hours. FIG. 16a shows the cylindrical implants placed into the hard acrylic block. FIG. 16b shows a diagram showing the implants, pre-made holes and bone cement used to retain the implants in the acrylic block. FIG. 16c shows the implants being pushed. The testing machine (Instron 5544 electromechanical testing system, Instron, Canton, Mass.) equipped with a 2000 N load cell and a pushing rod (diameter=0.8 mm) was used to load the implant vertically downward at a crosshead speed of 1 mm/min (FIG. 16c). The push-out value was determined by measuring the peak of load-displacement curve (FIG. 16d). FIG. 16d shows the load-displacement curve during the push-out test. The breakage strength, which was highest load of the curve, was measured as an implant push-out value.

Statistical Analysis.

Two-way ANOVA was used to assess the effect of titanium surface roughness and light treatment on the implant push-out value. T-test was used to examine differences between the untreated control and treated experimental group; <0.05 was considered statistically significant.

Result

Super-Hydrophilic Titanium Induced by Light Treatment.

The spread area of 10 µl water drop dramatically increased after UV treatment for both machined (13 times) and acid-etched surface (30 times) (FIG. 17). The contact angle of water before treatment, which was 69.9° and 88.4° for the machined and acid-etched surface, respectively, plummeted to 0.0±0.0° after UV irradiation, indicating the emergence of super-hydrophilic surfaces. In the test shown by FIG. 17, the hydrophilicity was evaluated by the spread area (the top views of titanium discs) and the contact angle (the side views of titanium discs) of 10 µl droplets of distilled water. Note that the contact angle is 0.0±0.0° (super-hydrophilic) after UV irradiation on the both surface topographies. Data are shown as the mean±SD (n=3) ("*" indicates that the data are statistically significant between the UV treated titanium and non-treated control, p<0.0001).

Surface Characteristics of Titanium after Light Treatment.

Figure 18A:
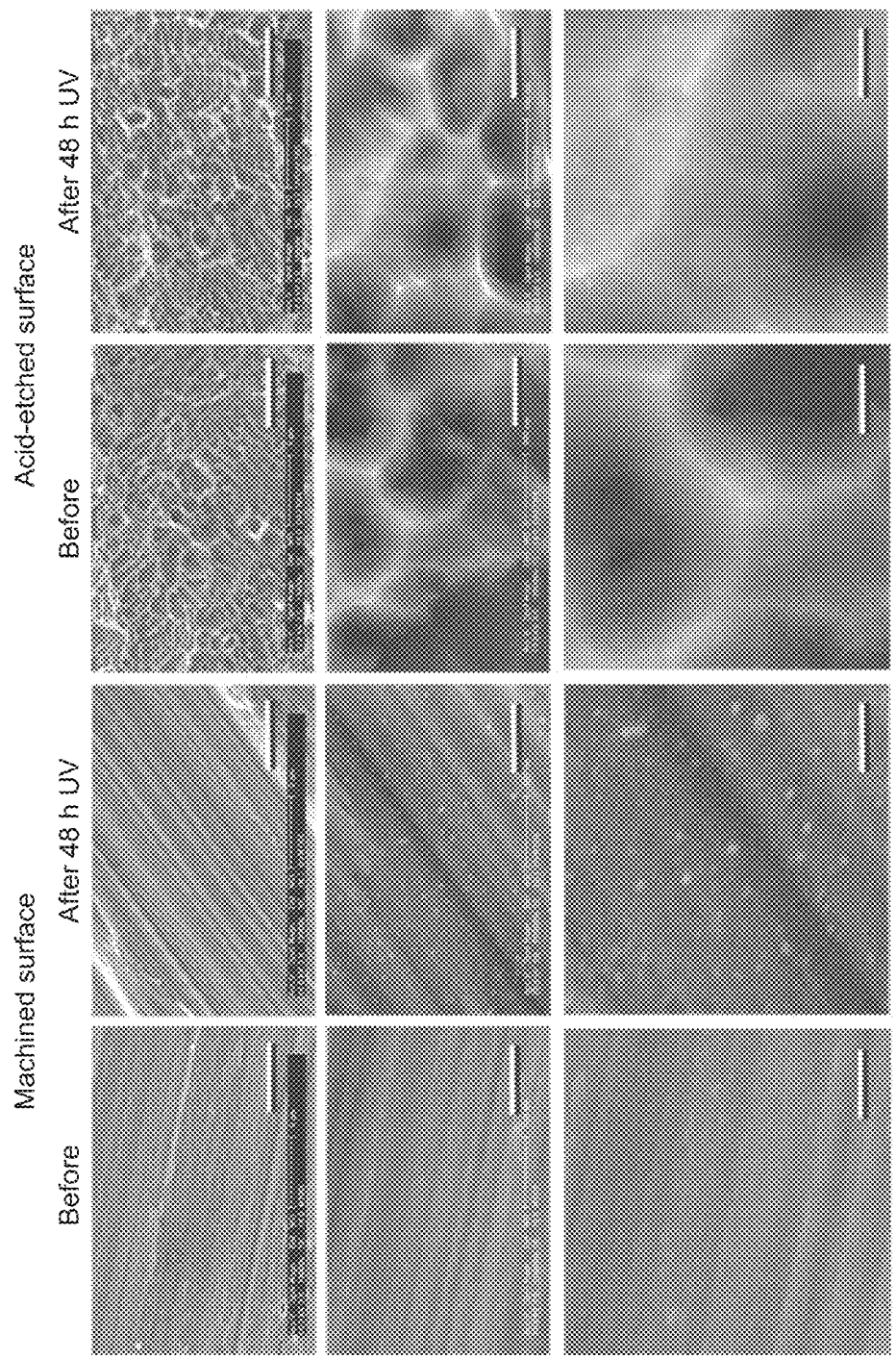

Scanning electron microscopy (SEM) examination showed isotropically and concentrically turned ridges on the machined surface before the light treatment (FIG. 18a), whereas the acid-etched surface was uniformly roughened. High magnification SEM revealed the emergence of nanospheres on the both titanium surfaces after the light treatment. The size of the nanospheres ranged 10-70 nm in diameter. Two-dimensional AFM images also revealed the nanometer-scale changes of contrast on the light-treated surfaces of the machined and acid-etched titanium (FIG. 18b). The circular contrasts ranged 50-600 nm in diameter. Both surface types were composed of commercially pure Ti with no contamination as shown by an energy dispersive X-ray (EDX) analysis (FIG. 18c). FIG. 18a shows scanning electron micrographs. FIG. 18b shows atomic force micrographs (AFM). FIG. 18c shows energy dispersive spectroscopic elemental spectrums of the machined and acid-etched surfaces before and after the light treatment. Bar=5 µm in the top panels, 500 µm in the mid panels, and 200 nm in the bottom panels of FIG. 18a Increased Bone Cement Wettability on Titanium by Light Treatment.

Figure 19:
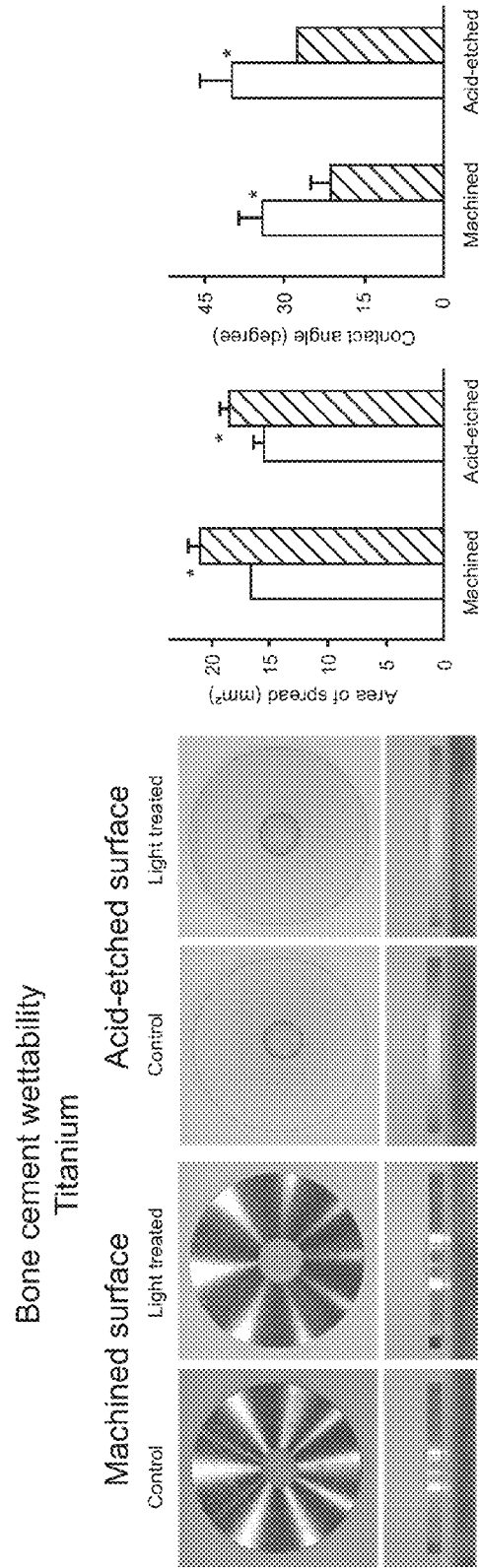
FIG. 19 shows an ultraviolet UV light-induced change of bone cement wettability of titanium.

The area of bone cement spread increased by 30% and 20% on the light treated machined titanium and acid-etched titanium compared to the untreated ones, respectively (FIG. 19). The contact angle of the bone cement was decreased after the light treatment, confirming the enhanced wettability of bone cement by the light treatment. In the test shown by FIG. 19, the bone cement-philicity was evaluated by the spread area (the top views of titanium discs) and the contact angle (the side views of titanium discs) of 10 µl droplets of the bone cement. Data are shown as the mean±SD (n=3) ("*" indicates that the data are statistically significant between the UV treated titanium and non-treated control, p<0.001).

Increased Bone Cement-Titanium Interfacial Bonding Strength by Light Treatment of Titanium.

Figure 20:
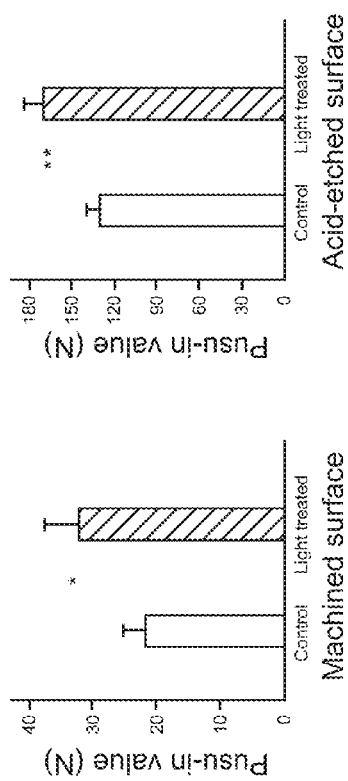
FIG. 20 shows push-out value of the machined and acid-etched implants with or without light treatment.

The bone cement-titanium interfacial strength measured by the push-out value was increased by the light-treatment of titanium implants for both machined (p<0.05, t-test) and acid-etched (p<0.01, t-test) surfaces (FIG. 20). In FIG. 20, data are shown as the mean±SD (n=6) (Statistically significant between the light-treated implants and untreated control, "*" indicating p<0.05; "**" indicating p<0.1). The increase was 40% for the machined surface and 25% for the acid-etched surface. The push-out values were higher for the acid-etched surfaces than for the machined surfaces (p<0.0001, 2-way ANOVA).

Increased Bone Cement Wettability on Titanium Alloy by Light Treatment.

Figure 21:
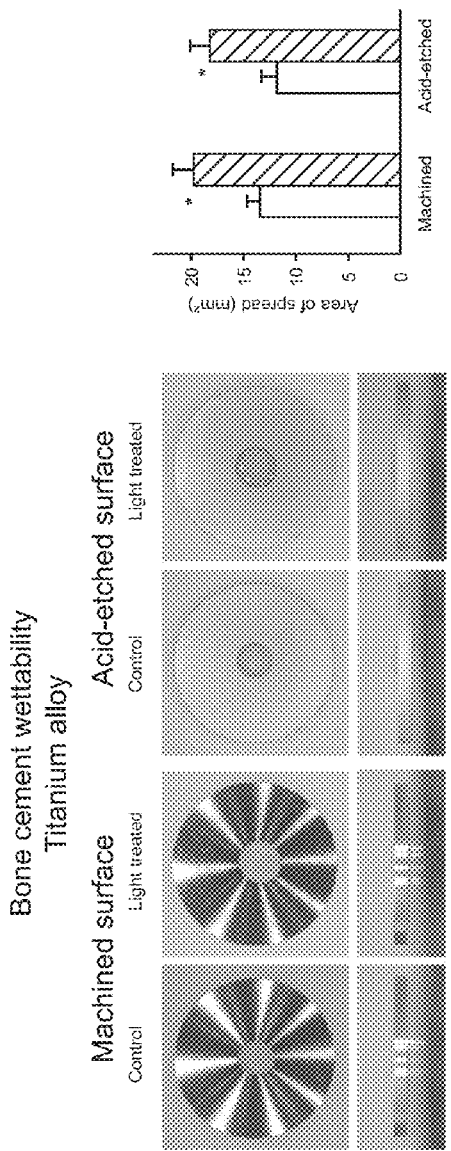
FIG. 21 shows an ultraviolet UV light-induced change of bone cement wettability on titanium alloy.

The area of bone cement spread was increased by the light treatment both on the machined and acid-etched titanium alloy, as seen on the pure titanium FIG. 21). The contact angle of the bone cement was decreased on the light treated titanium alloy compared to the untreated ones. In the test shown by FIG. 21, the bone cement-philicity was evaluated by the spread area (the top views of titanium discs) and the contact angle (the side views of titanium discs) of 10 µl droplets of the bone cement. Data are shown as the mean±SD (n=3) ("*" indicates that the data are statistically significant between the UV treated titanium and non-treated control, p<0.001).

Example 5

Nano-Scale and Micro-Scale Structural Changes of Titanium Implant by Light Treatment Methods Titanium Samples, Surface Analysis and Ultraviolet UV Light Irradiation. Two surface types of commercially pure titanium were prepared for cylindrical implants (1 mm in diameter and 2 mm in length) and disks (20 mm in diameter and 1.5 mm in thickness). One had a machined surface, turned by a lathe. The other was dual acid-etched with $H_2SO_4$ and HCl. Surface morphology was examined by scanning electron microscopy (SEM) (JSM-5900LV, Joel Ltd, Tokyo, Japan) and atomic force microscopy (SPM-9500J3, Shimadzu, Tokyo, Japan). The average roughness (Ra), root mean square roughness (Rrms) and peak-to-valley (Rp-v) were calculated. Titanium discs and cylindrical implants were treated with 0.1 mW/cm2 UVA and 0.03 mW/cm2 UVB for 48 hours or 1 week with air ventilation.

Animal Surgery.

Ten 8-week-old male Sprague-Dawley rats were anesthetized with 1-2% isoflurane inhalation. After their legs were shaved and scrubbed with 10% providone-iodine solution, the distal aspects of the femurs were carefully exposed via skin incision and muscle dissection. The flat surfaces of the distal femurs were selected for implant placement. The implant site was prepared 9 mm from the distal edge of the femur by drilling with a 0.8 mm round burr followed by reamers #ISO 090 and 100. Profuse irrigation with sterile isotonic saline solution was used for cooling and cleaning. One untreated cylindrical implant and one UV treated implant were placed into the right and left femurs, respectively. Implant stability was confirmed with a passive mechanical fit. Surgical sites were then closed in layers. Muscle and skin were sutured separately with resorbable suture thread. The University of California at Los Angeles (UCLA) Chancellor's Animal Research Committee approved this protocol and all experimentation was performed in accordance with the United States Department of Agriculture (USDA) guidelines of animal research.

Implant Biomechanical Push-in Test.

This method to assess biomechanical strength of bone-implant integration is described elsewhere (see, e.g., Ogawa, T., et al., J. Dent. Res., 79:1857-63 (2000)). Femurs containing a cylindrical implant were harvested and embedded immediately in auto-polymerizing resin with the top surface of the implant level. The testing machine (Instron 5544 electromechanical testing system, Instron, Canton, Mass.) equipped with a 2000 N load cell and a pushing rod (diameter=0.8 mm) was used to load the implant vertically downward at a crosshead speed of 1 mm/min. The push-in value was determined by measuring the peak of load-displacement curve.

Results

Nano-Scale Structural Changes of Titanium by Light Treatment.

Figures 22A, 22B:
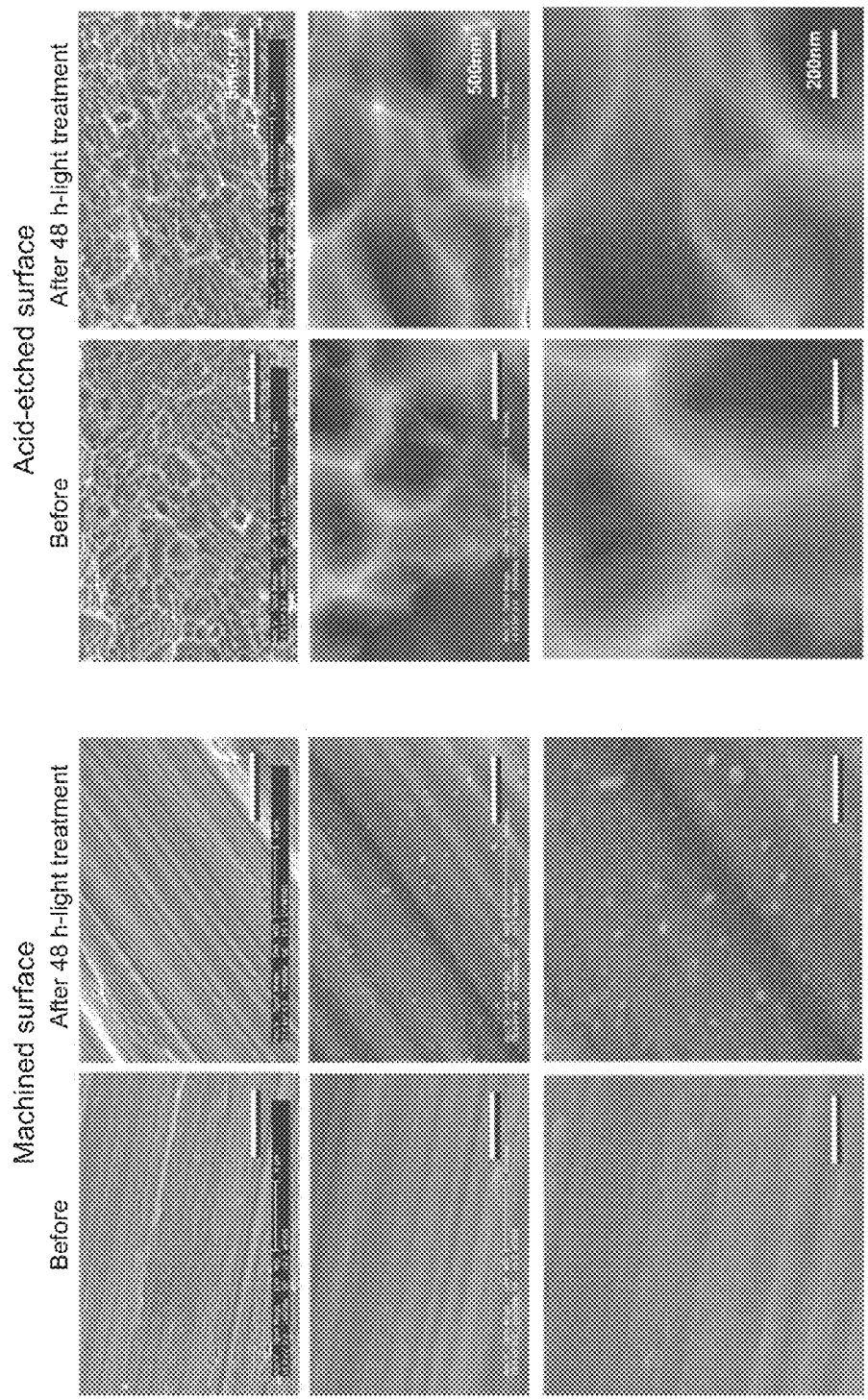
FIG. 22a-22d show the surface morphology and elemental composition of titanium surfaces used in this study, before and after ultra violet UV light treatment.

Scanning electron microscopy (SEM) examination showed isotropically and concentrically turned ridges on the machined surface before the light treatment (FIG. 22a). FIG. 22a shows the scanning electron micrographs of the machined titanium surface before and after the 48-hour light treatment. After 48 hours of the UV light treatment, nanospherical structures emerged on the machined surface. The size of the nanospheres ranged 10-70 nm in diameter. The acid-etched surface was uniformly roughened before the light-treatment (FIG. 22b). The 48 hour-light treatment induced the nanospheres on the entire acid-etched surface. FIG. 22b shows the scanning electron micrographs of the acid-etched titanium surface before and after the 48-hour light treatment.

Micron-Scale Structural Changes of Titanium by Light Treatment.

Figure 22C:
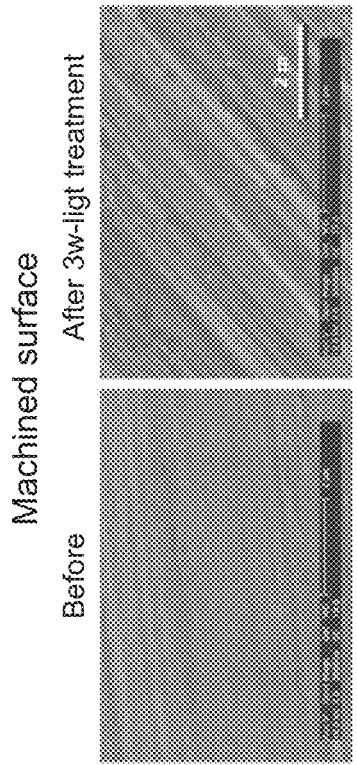

SEM observation reveled that the machined titanium surface showed the rougher surface after the 3-week light treatment (FIG. 22c). Some of the areas show the remaining nanospheres. FIG. 22c shows the scanning electron micrographs of the machined titanium surface before and after the 3-week light activation.

Figure 22D:
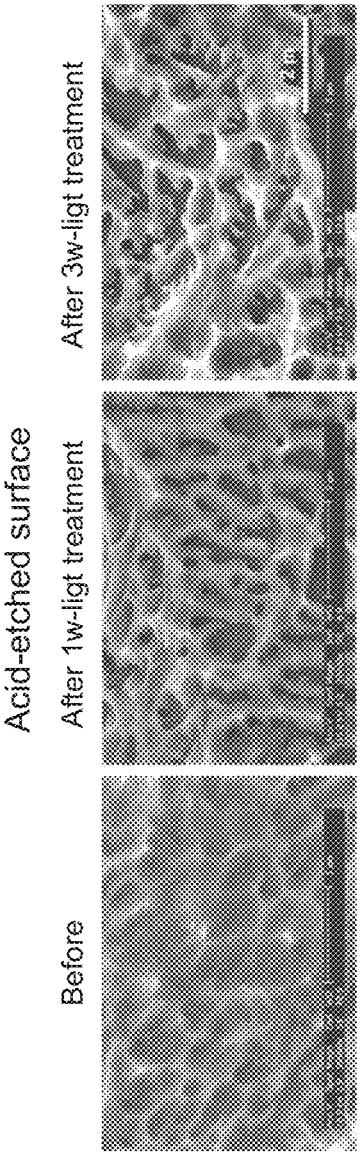

In contrast, the rough surface of the acid-etched titanium having sharp peaks and valleys changed its topographical properties with rounded peaks and large inter-peak distance after 1-week or 3-week light treatment (FIG. 22d). FIG. 22d shows the scanning electron micrographs of the acid-etched titanium surface before and after 1-week and 3-week light treatments. Nanoscale structures recognizable between the peaks before the light treatment appeared less after the longer light treatment. The newly generated rounded convexities appeared roof-like structure, resulting in the creation of undercut space underneath the structure.

Average roughness (Ra), maximum peak-to-valley length (Rp-v) and inter-irregularities space (Sm) were 0.024±0.005 μm, 0.149±0.064 μm, and 0.659±0.261 μm, respectively, for the machined surface, and 0.022±0.008 μm, 0.237±0.070 μm, and 0.934±0.174 μm, respectively, for the light-treated machined surface, and 0.231±0.051 μm, 1.190±0.380 μm, and 1.163±0.252 respectively, for the acid-etched surface, and 0.097±0.016 μm, 0.846±0.082 μm, and 2.014±0.399 μm, respectively, for the light-treated acid-etched surface. The light-treated machined surface showed higher peak-to-valley length (Rp-v) and inter-irregularities space (Sm) than the untreated control, while the light-treated acid-etched surface showed lower average roughness (Ra) and maximum peak-to-valley length (Rp-v), but higher inter-irregularities space (Sm) than the untreated control ($p<0.05$, t-test). These quantified results agreed with the morphological observation described above and indicate that the light-treatment alters the surface topography differently depending on the original surface topographies.

Light Treatment Accelerates and Enhances Titanium Implant Stabilization.

Figure 23:
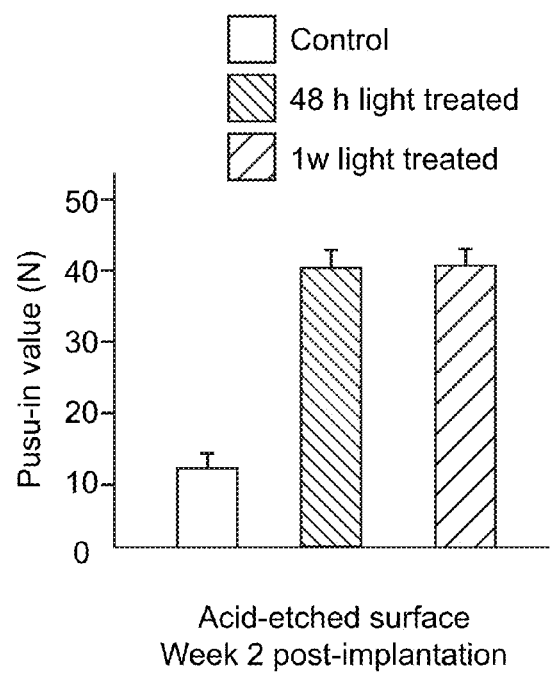
FIG. 23 shows the light-enhanced bone-titanium integration evaluated by biomechanical push-in test.

In vivo establishment of implant stability should be a most pertinent variable that reflects clinical capacity of implants as a load-bearing device. In vivo stability of titanium implants with or without light treatment was examined using the established biomechanical implant push-in test in the rat model (see, e.g., Ogawa, T., et al., J. Dent. Res., 79:1857-63 (2000)). The push-in value at 2 weeks post-implantation soared approximately 3 times for both 48-hour and 1-week light-treated acid-etched titanium implants compared to the untreated control acid-etched titanium implants (FIG. 23). In the test shown by FIG. 23, acid-etched titanium implants with or without light activation were placed into the rat femur, and the femur specimen with the implants were harvested and embedded into the metheylmethacrylate block. Biomechanical stability of the implants was, then, evaluated at 2 week post-implantation by measuring the breakage strength against push-in load. Data are shown as the mean±SD (n=5) (the symbol "*" indicates that the data are statistically significant between the light-treated groups and untreated control, $p<0.0001$).

Example 6

Light-Activation on Zirconium Implants

UV light-improved hydrophilicity and osteoconductivity of zirconium surface. The possible light-inducible changes in wettability (hydrophilicity) of zirconium oxide were examined as follows. Following light treatment for 48 hours at a level of 0.1 mW/cm$^2$ UVA and 0.03 mW/cm$^2$ UVB, the wettability was evaluated by the contact angle that water drops formed. The contact angle of 10 μl water drop dramatically decreased to the level around 5 degree after light treatment (FIG. 24a), indicating the creation of superhydrophilic surface by the light treatment out of the hydrophobic surface. After the UV-light treatment, the surface morphology change on zirconium. SEM examination reveealed that the light-treated zirconium surface was rougher than the non-treated one, consisting of more nanoscale spherical, cone or pyramid-shaped nanostructures. The size of the nanostructures ranged from about 10 nm to 1,000 nm.

In the test shown by FIG. 24a, the hydrophilicity was evaluated by the contact angle (the side views of the zirconium discs) of 10 μl droplets of distilled water. Data are shown as the mean±SD (n=3) ("*" indicates that the data are statistically significant between the UV treated zirconium and non-treated zirconium, $p<0.0001$).

The proliferative potential of osteoblasts on the light-treated zirconium surface was investigated. To evaluate the cell proliferation, the rat bone marrow-derived osteoblasts were inoculated onto the zirconium disks with or without light treatment. The pre-treatment of UV light significantly increased the cell proliferation by up to 100% (FIG. 24b). FIG. 24b shows cell-philic zirconium surfaces created by ultraviolet UV light treatment. The proliferation was evaluated by the cell density of the rat bone marrow stem cell-derived osteoblasts. The machined zirconium dioxide discs with or without UV treatment were placed horizontally in the polystyrene culture dish. The cells at the different time points of culture were trypsinized and counted using hematocytometer. Data are shown as the mean±SD (n=3) ("*" indicates that the data are statistically significant between the light treated and untreated control, $p<0.0001$).

The gene expression of an osteoblastic differentiation marker was also examined by RT-PCR (reverse transcriptase-polymerase chain reaction) in bone marrow-derived osteoblastic cultures on zirconium (FIG. 24c). Osteopontin expression slightly increased or remained the same level between the light-treated and untreated surfaces from day 3 to 14, indicating that light treatment on zirconium increases osteoblastic proliferation while not compromising the differentiation capacity. FIG. 24c shows expression of osteopontin gene after ultraviolet light treatment on zirconium surface. The osteoblasts were cultured on zirconium oxide with or without light treatment, and the gene expression was assessed using a reverse transcriptase-polymerase chain reaction (RT-PCR). The quantified expression level of osteopontin gene relative to the level of GAPDH mRNA expression is presented.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A method of treating a metallic implant for enhancing tissue integration capability of the implant, comprising:

roughening surface of the implant by at least one of a physical or chemical treatment; and irradiating the roughened implant with ultraviolet light;

wherein the ultraviolet light causes the roughed surface to form nanoconstructs having a size in the range of about 10 nm to about 70 nm in diameter, and wherein the nanoconstructs comprise nano-hemespherical nodules, nanocones, nanopyramids, or combinations thereof.

2. The method of claim 1 wherein the nanoconstructs have a size from about 20 nm to about 50 nm in diameter.

3. The method of claim 2, wherein the metallic implant is selected from the group consisting of tooth implants, jaw bone implant, repairing and stabilizing screws, pins and plates for bone, spinal implants, femoral implants, neck implants, knee implants, wrist implants, joint implants such as an artificial hip joint, maxillofacial implants such as ear and nose implants, limb prostheses for conditions resulting from injury and disease, and combinations thereof.

4. The method of claim 1, wherein the physical treatment is machining, sand-blasting, or metallic or nonmetallic deposition, and wherein the chemical treatment is acid-etching, sand-blasting, oxidation, or alkaline treatment.

5. The method of claim 4, wherein the metallic implant is selected from the group consisting of tooth implants, jaw bone implant, repairing and stabilizing screws, pins and plates for bone, spinal implants, femoral implants, neck implants, knee implants, wrist implants, joint implants such as an artificial hip joint, maxillofacial implants such as ear and nose implants, limb prostheses for conditions resulting from injury and disease, and combinations thereof.

6. The method of claim 1, wherein the UV light is at a level of 0.1 mW/cm$^2$ UVA and 0.03 mW/cm$^2$ UVB.

7. The method of claim 6, wherein the metallic implant is selected from the group consisting of tooth implants, jaw bone implant, repairing and stabilizing screws, pins and plates for bone, spinal implants, femoral implants, neck implants, knee implants, wrist implants, joint implants such as an artificial hip joint, maxillofacial implants such as ear and nose implants, limb prostheses for conditions resulting from injury and disease, and combinations thereof.

8. The method of claim 1, wherein the metallic implant comprises gold, platinum, titanium, tantalum, niobium, nickel, iron, chromium, cobalt, zirconium, magnesium, aluminum, palladium, an alloy formed thereof, or combinations thereof.

9. The method of claim 8, wherein the metallic implant is selected from the group consisting of tooth implants, jaw bone implant, repairing and stabilizing screws, pins and plates for bone, spinal implants, femoral implants, neck implants, knee implants, wrist implants, joint implants such as an artificial hip joint, maxillofacial implants such as ear and nose implants, limb prostheses for conditions resulting from injury and disease, and combinations thereof.

10. The method of claim 1, wherein the metallic implant is a titanium implant.

11. The method of claim 10, wherein the metallic implant is selected from the group consisting of tooth implants, jaw bone implant, repairing and stabilizing screws, pins and plates for bone, spinal implants, femoral implants, neck implants, knee implants, wrist implants, joint implants such as an artificial hip joint, maxillofacial implants such as ear and nose implants, limb prostheses for conditions resulting from injury and disease, and combinations thereof.

12. The method of claim 1, wherein the medical implant is a zirconium implant or chromium-cobalt alloy implant.

13. The method of claim 12, wherein the metallic implant is selected from the group consisting of tooth implants, jaw bone implant, repairing and stabilizing screws, pins and plates for bone, spinal implants, femoral implants, neck implants, knee implants, wrist implants, joint implants such as an artificial hip joint, maxillofacial implants such as ear and nose implants, limb prostheses for conditions resulting from injury and disease, and combinations thereof.

14. The method of claim 1, wherein the metallic implant is selected from the group consisting of tooth implants, jaw bone implant, repairing and stabilizing screws, pins and plates for bone, spinal implants, femoral implants, neck implants, knee implants, wrist implants, joint implants such as an artificial hip joint, maxillofacial implants such as ear and nose implants, limb prostheses for conditions resulting from injury and disease, and combinations thereof.

15. The method of claim 1, wherein the metallic implant is selected from the group consisting of tooth implants, jaw bone implant, repairing and stabilizing screws, pins and plates for bone, spinal implants, femoral implants, neck implants, knee implants, wrist implants, joint implants such as an artificial hip joint, maxillofacial implants such as ear and nose implants, limb prostheses for conditions resulting from injury and disease, and combinations thereof.

* * * * *